(12) United States Patent
Podhajsky

(10) Patent No.: US 8,486,061 B2
(45) Date of Patent: Jul. 16, 2013

(54) IMAGINARY IMPEDANCE PROCESS MONITORING AND INTELLIGENT SHUT-OFF

(75) Inventor: Ronald J. Podhajsky, Boulder, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/593,550

(22) Filed: Aug. 24, 2012

(65) Prior Publication Data
US 2012/0316556 A1  Dec. 13, 2012

Related U.S. Application Data

(60) Division of application No. 12/477,245, filed on Jun. 3, 2009, now Pat. No. 8,262,652, which is a continuation-in-part of application No. 12/351,935, filed on Jan. 12, 2009, now Pat. No. 8,167,875, and a continuation-in-part of application No. 12/351,970, filed on Jan. 12, 2009, now Pat. No. 8,152,802, and a continuation-in-part of application No. 12/351,960, filed on Jan. 12, 2009, now Pat. No. 8,162,932.

(51) Int. Cl.
*A61B 18/04* (2006.01)

(52) U.S. Cl.
USPC ............................................. 606/38; 606/34

(58) Field of Classification Search
USPC ..................................................... 606/34, 38
See application file for complete search history.

(56) References Cited

U.S. PATENT DOCUMENTS

| | | | |
|---|---|---|---|
| 1,787,709 A | 1/1931 | Wappler | |
| 1,813,902 A | 7/1931 | Bovie | |
| 1,841,968 A | 1/1932 | Lowry | |
| 1,863,118 A | 6/1932 | Liebel | |
| 1,945,867 A | 2/1934 | Rawls | |
| 2,693,106 A | 6/1951 | Henry | |
| 2,827,056 A | 3/1958 | Degelman | |
| 2,849,611 A | 8/1958 | Adams | |
| 2,883,198 A | 4/1959 | Narumi | |
| 3,001,132 A | 9/1961 | Britt | |
| 3,058,470 A | 10/1962 | Seeliger et al. | |
| 3,089,496 A | 5/1963 | Degelman | |
| 3,154,365 A | 10/1964 | Crimmins | |
| 3,163,165 A | 12/1964 | Islikawa | |
| 3,252,052 A | 5/1966 | Nash | |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

Smith, S. W. The scientist and engineer\'s guide to digital signal processing. 1st. California Technical Pub, 1997.*

(Continued)

*Primary Examiner* — Linda Dvorak
*Assistant Examiner* — Jaymi Della

(57) ABSTRACT

An electrosurgical generator for supplying electrosurgical energy to tissue is disclosed. The generator includes sensor circuitry configured to measure an imaginary impedance and/or a rate of change of the imaginary impedance of tissue. The generator also includes a controller configured to regulate output of the electrosurgical generator based on the measured imaginary impedance and/or the rate of change of the imaginary impedance.

7 Claims, 7 Drawing Sheets

U.S. PATENT DOCUMENTS

| | | |
|---|---|---|
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,019 A | 10/1973 | Podowski |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,908,176 A | 9/1975 | De Boer et al. |
| 3,913,583 A | 10/1975 | Bross |
| 3,923,063 A | 12/1975 | Andrews et al. |
| 3,933,157 A | 1/1976 | Bjurwill et al. |
| 3,938,072 A | 2/1976 | Baird et al. |
| 3,944,936 A | 3/1976 | Pryor |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 3,998,538 A | 12/1976 | Urso et al. |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,153,880 A | 5/1979 | Navratil |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gosner |
| 4,204,549 A | 5/1980 | Paglione |
| 4,209,018 A | 6/1980 | Meinke et al. |
| 4,228,809 A | 10/1980 | Paglione |
| 4,229,714 A | 10/1980 | Yu |
| 4,231,372 A | 11/1980 | Newton |
| 4,232,676 A | 11/1980 | Herczog |
| 4,237,887 A | 12/1980 | Gosner |
| 4,247,815 A | 1/1981 | Larsen et al. |
| 4,271,837 A | 6/1981 | Schuler |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,359,626 A | 11/1982 | Potter |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,430,625 A | 2/1984 | Yokoyama |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,532,924 A | 8/1985 | Auth et al. |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,572,190 A | 2/1986 | Azam et al. |
| 4,580,575 A | 4/1986 | Birnbaum et al. |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Paterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,741,348 A | 5/1988 | Kikuchi et al. |
| 4,744,372 A | 5/1988 | Kikuchi et al. |
| 4,754,757 A | 7/1988 | Feucht |
| 4,767,999 A | 8/1988 | VerPlanck |
| 4,768,969 A | 9/1988 | Bauer et al. |
| 4,785,829 A | 11/1988 | Convert et al. |
| 4,788,634 A | 11/1988 | Schlecht et al. |
| 4,805,621 A | 2/1989 | Heinze et al. |

| | | | | | |
|---|---|---|---|---|---|
| 4,818,954 A | 4/1989 | Flachenecker et al. | 5,342,357 A | 8/1994 | Nardella |
| 4,827,927 A | 5/1989 | Newton | 5,342,409 A | 8/1994 | Mullett |
| 4,848,335 A | 7/1989 | Manes | 5,346,406 A | 9/1994 | Hoffman et al. |
| 4,860,745 A | 8/1989 | Farin et al. | 5,346,491 A | 9/1994 | Oertli |
| 4,862,889 A | 9/1989 | Feucht | 5,348,554 A | 9/1994 | Imran et al. |
| 4,887,199 A | 12/1989 | Whittle | 5,354,325 A | 10/1994 | Chive et al. |
| 4,890,610 A | 1/1990 | Kirwan et al. | 5,364,392 A | 11/1994 | Warner et al. |
| 4,903,696 A | 2/1990 | Stasz et al. | 5,369,567 A | 11/1994 | Furuta et al. |
| 4,907,589 A | 3/1990 | Cosman | 5,370,645 A | 12/1994 | Klicek et al. |
| 4,922,210 A | 5/1990 | Flachenecker et al. | 5,370,672 A | 12/1994 | Fowler et al. |
| 4,925,089 A | 5/1990 | Chaparro et al. | 5,370,675 A | 12/1994 | Edwards et al. |
| 4,931,047 A | 6/1990 | Broadwin et al. | 5,372,596 A | 12/1994 | Klicek et al. |
| 4,931,717 A | 6/1990 | Gray et al. | 5,383,874 A | 1/1995 | Jackson |
| 4,938,761 A | 7/1990 | Ensslin | 5,383,876 A | 1/1995 | Nardella |
| 4,942,313 A | 7/1990 | Kinzel | 5,383,917 A | 1/1995 | Desai et al. |
| 4,959,606 A | 9/1990 | Forge | 5,385,148 A | 1/1995 | Lesh et al. |
| 4,961,047 A | 10/1990 | Carder | 5,396,194 A | 3/1995 | Williamson et al. |
| 4,961,435 A | 10/1990 | Kitagawa et al. | 5,400,267 A | 3/1995 | Denen et al. |
| 4,966,597 A | 10/1990 | Cosman | 5,403,311 A | 4/1995 | Abele et al. |
| 4,969,885 A | 11/1990 | Farin | 5,403,312 A | 4/1995 | Yates et al. |
| 4,992,719 A | 2/1991 | Harvey | 5,409,000 A | 4/1995 | Imran |
| 4,993,430 A | 2/1991 | Shimoyama et al. | 5,409,485 A | 4/1995 | Suda |
| 4,995,877 A | 2/1991 | Ams et al. | 5,413,573 A | 5/1995 | Koivukangas |
| 5,015,227 A | 5/1991 | Broadwin et al. | 5,414,238 A | 5/1995 | Steigerwald et al. |
| 5,024,668 A | 6/1991 | Peters et al. | 5,417,719 A | 5/1995 | Hull et al. |
| 5,044,977 A | 9/1991 | Vindigni | 5,422,567 A | 6/1995 | Matsunaga |
| 5,057,105 A | 10/1991 | Malone et al. | 5,422,926 A | 6/1995 | Smith et al. |
| 5,067,953 A | 11/1991 | Feucht | 5,423,808 A | 6/1995 | Edwards et al. |
| 5,075,839 A | 12/1991 | Fisher et al. | 5,423,809 A | 6/1995 | Klicek |
| 5,078,153 A | 1/1992 | Nordlander et al. | 5,423,810 A | 6/1995 | Goble et al. |
| 5,087,257 A | 2/1992 | Farin | 5,423,811 A | 6/1995 | Imran et al. |
| 5,099,840 A | 3/1992 | Goble et al. | 5,425,704 A | 6/1995 | Sakurai et al. |
| 5,103,804 A | 4/1992 | Abele et al. | 5,429,596 A | 7/1995 | Arias et al. |
| 5,108,389 A | 4/1992 | Cosmescu | 5,430,434 A | 7/1995 | Lederer et al. |
| 5,108,391 A | 4/1992 | Flachenecker | 5,432,459 A | 7/1995 | Thompson |
| 5,113,116 A | 5/1992 | Wilson | 5,433,739 A | 7/1995 | Sluijter et al. |
| 5,119,284 A | 6/1992 | Fisher et al. | 5,436,566 A | 7/1995 | Thompson |
| 5,122,137 A | 6/1992 | Lennox | 5,438,302 A | 8/1995 | Goble |
| 5,133,711 A | 7/1992 | Hagen | 5,443,462 A | 8/1995 | Hannant |
| 5,151,102 A | 9/1992 | Kamiyama et al. | 5,443,463 A | 8/1995 | Stern et al. |
| 5,152,762 A | 10/1992 | McElhenney | 5,445,635 A | 8/1995 | Denen et al. |
| 5,157,603 A | 10/1992 | Scheller et al. | 5,445,638 A | 8/1995 | Rydell et al. |
| 5,160,334 A | 11/1992 | Billings et al. | 5,448,466 A | 9/1995 | Erckert |
| 5,161,893 A | 11/1992 | Shigezawa et al. | 5,451,224 A | 9/1995 | Goble et al. |
| 5,167,658 A | 12/1992 | Ensslin | 5,452,725 A | 9/1995 | Martenson |
| 5,167,659 A | 12/1992 | Ohtomo et al. | 5,454,809 A | 10/1995 | Janssen |
| 5,190,517 A | 3/1993 | Zieve et al. | 5,458,597 A | 10/1995 | Edwards et al. |
| 5,196,008 A | 3/1993 | Kuenecke | 5,462,521 A | 10/1995 | Brucker et al. |
| 5,196,009 A | 3/1993 | Kirwan, Jr. | 5,472,441 A | 12/1995 | Edwards et al. |
| 5,201,900 A | 4/1993 | Nardella | 5,472,443 A | 12/1995 | Cordis et al. |
| 5,207,691 A | 5/1993 | Nardella | 5,474,464 A | 12/1995 | Drewnicki |
| 5,216,338 A | 6/1993 | Wilson | 5,480,399 A | 1/1996 | Hebborn |
| 5,230,623 A | 7/1993 | Guthrie et al. | 5,483,952 A | 1/1996 | Aranyi |
| 5,233,515 A | 8/1993 | Cosman | 5,496,312 A | 3/1996 | Klicek |
| 5,234,427 A | 8/1993 | Ohtomo et al. | 5,496,313 A | 3/1996 | Gentelia et al. |
| 5,244,462 A | 9/1993 | Delahuerga et al. | 5,496,314 A | 3/1996 | Eggers |
| 5,249,121 A | 9/1993 | Baum et al. | 5,498,261 A | 3/1996 | Strul |
| 5,249,585 A | 10/1993 | Turner et al. | 5,500,012 A | 3/1996 | Brucker et al. |
| 5,254,117 A | 10/1993 | Rigby et al. | 5,500,616 A | 3/1996 | Ochi |
| RE34,432 E | 11/1993 | Bertrand | 5,511,993 A | 4/1996 | Yamada et al. |
| 5,267,994 A | 12/1993 | Gentelia et al. | 5,514,129 A | 5/1996 | Smith |
| 5,267,997 A | 12/1993 | Farin | 5,520,684 A | 5/1996 | Imran |
| 5,269,780 A | 12/1993 | Roos | 5,531,774 A | 7/1996 | Schulman et al. |
| 5,271,413 A | 12/1993 | Dalamagas et al. | 5,534,018 A | 7/1996 | Wahlstrand et al. |
| 5,281,213 A | 1/1994 | Milder et al. | 5,536,267 A | 7/1996 | Edwards et al. |
| 5,282,840 A | 2/1994 | Hudrlik | 5,540,677 A | 7/1996 | Sinofsky |
| 5,290,283 A | 3/1994 | Suda | 5,540,681 A | 7/1996 | Strul et al. |
| 5,295,857 A | 3/1994 | Toly | 5,540,682 A | 7/1996 | Gardner et al. |
| 5,300,068 A | 4/1994 | Rosar et al. | 5,540,683 A | 7/1996 | Ichikawa |
| 5,300,070 A | 4/1994 | Gentelia | 5,540,684 A | 7/1996 | Hassler, Jr. |
| 5,304,917 A | 4/1994 | Somerville | 5,541,376 A | 7/1996 | Ladtkow et al. |
| 5,318,563 A | 6/1994 | Malis et al. | 5,542,916 A | 8/1996 | Hirsch et al. |
| 5,323,778 A | 6/1994 | Kandarpa et al. | 5,545,161 A | 8/1996 | Imran |
| 5,324,283 A | 6/1994 | Heckele | 5,554,172 A | 9/1996 | Horner et al. |
| 5,330,518 A | 7/1994 | Neilson et al. | 5,556,396 A | 9/1996 | Cohen et al. |
| 5,334,183 A | 8/1994 | Wuchinich | 5,558,671 A | 9/1996 | Yates |
| 5,334,193 A | 8/1994 | Nardella | 5,559,688 A | 9/1996 | Pringle |
| 5,341,807 A | 8/1994 | Nardella | 5,562,720 A | 10/1996 | Stern et al. |
| 5,342,356 A | 8/1994 | Ellman | 5,569,242 A | 10/1996 | Lax et al. |

| | | |
|---|---|---|
| 5,571,147 A | 11/1996 | Sluijter et al. |
| 5,573,533 A | 11/1996 | Strul |
| 5,584,830 A | 12/1996 | Ladd et al. |
| 5,588,432 A | 12/1996 | Crowley |
| 5,596,466 A | 1/1997 | Ochi |
| 5,596,995 A | 1/1997 | Sherman et al. |
| 5,599,344 A | 2/1997 | Paterson |
| 5,599,345 A | 2/1997 | Edwards et al. |
| 5,599,348 A | 2/1997 | Gentelia et al. |
| 5,605,150 A | 2/1997 | Radons et al. |
| 5,609,560 A | 3/1997 | Ichikawa et al. |
| 5,613,966 A | 3/1997 | Makower et al. |
| 5,620,481 A | 4/1997 | Desai et al. |
| 5,626,575 A | 5/1997 | Crenner |
| 5,628,745 A | 5/1997 | Bek |
| 5,628,771 A | 5/1997 | Mizukawa et al. |
| 5,633,578 A | 5/1997 | Eggers et al. |
| 5,640,113 A | 6/1997 | Hu |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,664,953 A | 9/1997 | Reylek |
| 5,674,217 A | 10/1997 | Wahlstrom et al. |
| 5,675,609 A | 10/1997 | Johnson |
| 5,678,568 A | 10/1997 | Uchikubo et al. |
| 5,681,307 A | 10/1997 | McMahan |
| 5,685,840 A | 11/1997 | Schechter et al. |
| 5,688,267 A | 11/1997 | Panescu et al. |
| 5,693,042 A | 12/1997 | Bioarski et al. |
| 5,693,078 A | 12/1997 | Desai et al. |
| 5,694,304 A | 12/1997 | Telefus et al. |
| 5,695,494 A | 12/1997 | Becker |
| 5,696,441 A | 12/1997 | Mak et al. |
| 5,697,925 A | 12/1997 | Taylor |
| 5,697,927 A | 12/1997 | Imran et al. |
| 5,702,386 A | 12/1997 | Stern et al. |
| 5,702,429 A | 12/1997 | King |
| 5,707,369 A | 1/1998 | Vaitekunas et al. |
| 5,712,772 A | 1/1998 | Telefus et al. |
| 5,713,896 A | 2/1998 | Nardella |
| 5,718,246 A | 2/1998 | Vona |
| 5,720,742 A | 2/1998 | Zacharias |
| 5,720,744 A | 2/1998 | Eggleston et al. |
| 5,722,975 A | 3/1998 | Edwards et al. |
| 5,729,448 A | 3/1998 | Haynie et al. |
| 5,733,281 A | 3/1998 | Nardella |
| 5,735,846 A | 4/1998 | Panescu et al. |
| 5,738,683 A | 4/1998 | Osypka |
| 5,743,900 A | 4/1998 | Hara |
| 5,743,903 A | 4/1998 | Stern et al. |
| 5,749,869 A | 5/1998 | Lindenmeier et al. |
| 5,749,871 A | 5/1998 | Hood et al. |
| 5,755,715 A | 5/1998 | Stern |
| 5,762,609 A | 6/1998 | Benaron et al. |
| 5,766,153 A | 6/1998 | Eggers et al. |
| 5,766,165 A | 6/1998 | Gentelia et al. |
| 5,769,847 A | 6/1998 | Panescu |
| 5,772,659 A | 6/1998 | Becker et al. |
| 5,777,519 A | 7/1998 | Simopoulos |
| 5,788,688 A | 8/1998 | Bauer et al. |
| 5,792,138 A | 8/1998 | Shipp |
| 5,797,902 A | 8/1998 | Netherly |
| 5,797,941 A | 8/1998 | Schulze et al. |
| 5,807,253 A | 9/1998 | Dumoulin et al. |
| 5,810,804 A | 9/1998 | Gough et al. |
| 5,814,092 A | 9/1998 | King |
| 5,817,091 A | 10/1998 | Nardella et al. |
| 5,817,093 A | 10/1998 | Williamson, IV et al. |
| 5,820,568 A | 10/1998 | Willis |
| 5,827,271 A | 10/1998 | Bussey et al. |
| 5,830,212 A | 11/1998 | Cartmell |
| 5,831,166 A | 11/1998 | Kozuka et al. |
| 5,836,909 A | 11/1998 | Cosmescu |
| 5,836,943 A | 11/1998 | Miller, III |
| 5,836,990 A | 11/1998 | Li |
| 5,843,019 A | 12/1998 | Eggers et al. |
| 5,843,075 A | 12/1998 | Taylor |
| 5,846,236 A | 12/1998 | Lindenmeier et al. |
| 5,849,010 A | 12/1998 | Wurzer et al. |
| 5,853,409 A | 12/1998 | Swanson et al. |
| 5,860,832 A | 1/1999 | Wayt et al. |
| 5,865,788 A | 2/1999 | Edwards et al. |
| 5,868,737 A | 2/1999 | Taylor et al. |
| 5,868,739 A | 2/1999 | Lindenmeier et al. |
| 5,868,740 A | 2/1999 | LeVeen et al. |
| 5,871,481 A | 2/1999 | Kannenberg et al. |
| 5,891,142 A | 4/1999 | Eggers et al. |
| 5,893,848 A | 4/1999 | Negus et al. |
| 5,897,552 A | 4/1999 | Edwards et al. |
| 5,906,614 A | 5/1999 | Stern et al. |
| 5,908,444 A | 6/1999 | Azure |
| 5,913,882 A | 6/1999 | King |
| 5,921,982 A | 7/1999 | Lesh et al. |
| 5,925,070 A | 7/1999 | King et al. |
| 5,931,836 A | 8/1999 | Hatta et al. |
| 5,935,124 A | 8/1999 | Klumb et al. |
| 5,936,446 A | 8/1999 | Lee |
| 5,938,690 A | 8/1999 | Law et al. |
| 5,944,553 A | 8/1999 | Yasui et al. |
| 5,948,007 A | 9/1999 | Starkenbaum et al. |
| 5,951,545 A | 9/1999 | Schilling |
| 5,951,546 A | 9/1999 | Lorentzen |
| 5,954,686 A | 9/1999 | Garito et al. |
| 5,954,717 A | 9/1999 | Behl et al. |
| 5,954,719 A | 9/1999 | Chen et al. |
| 5,957,961 A | 9/1999 | Maguire et al. |
| 5,957,969 A | 9/1999 | Warner et al. |
| 5,959,253 A | 9/1999 | Shinchi |
| 5,961,344 A | 10/1999 | Rosales et al. |
| 5,961,871 A | 10/1999 | Bible et al. |
| 5,964,746 A | 10/1999 | McCary |
| 5,971,980 A | 10/1999 | Sherman |
| 5,971,981 A | 10/1999 | Hill et al. |
| 5,976,128 A | 11/1999 | Schilling et al. |
| 5,983,141 A | 11/1999 | Sluijter et al. |
| 5,999,848 A | 12/1999 | Gord et al. |
| 6,007,532 A | 12/1999 | Netherly |
| 6,010,499 A | 1/2000 | Cobb |
| 6,013,074 A | 1/2000 | Taylor |
| 6,014,581 A | 1/2000 | Whayne et al. |
| 6,017,338 A | 1/2000 | Brucker et al. |
| 6,017,354 A | 1/2000 | Culp et al. |
| 6,022,346 A | 2/2000 | Panescu et al. |
| 6,022,347 A | 2/2000 | Lindenmeier et al. |
| 6,033,399 A | 3/2000 | Gines |
| 6,039,731 A | 3/2000 | Taylor et al. |
| 6,039,732 A | 3/2000 | Ichikawa et al. |
| 6,041,260 A | 3/2000 | Stern et al. |
| 6,044,283 A | 3/2000 | Fein et al. |
| 6,053,910 A | 4/2000 | Fleenor |
| 6,053,912 A | 4/2000 | Panescu et al. |
| 6,055,458 A | 4/2000 | Cochran et al. |
| 6,056,745 A | 5/2000 | Panescu et al. |
| 6,056,746 A | 5/2000 | Goble et al. |
| 6,059,780 A | 5/2000 | Gough et al. |
| 6,059,781 A | 5/2000 | Yamanashi et al. |
| 6,063,075 A | 5/2000 | Mihori |
| 6,063,078 A | 5/2000 | Wittkampf |
| 6,066,137 A | 5/2000 | Greep |
| 6,068,627 A | 5/2000 | Orszulak et al. |
| 6,074,089 A | 6/2000 | Hollander et al. |
| 6,074,386 A | 6/2000 | Goble et al. |
| 6,074,388 A | 6/2000 | Tockweiler et al. |
| 6,080,149 A | 6/2000 | Huang et al. |
| 6,088,614 A | 7/2000 | Swanson |
| 6,089,864 A | 7/2000 | Buckner et al. |
| 6,090,123 A | 7/2000 | Culp et al. |
| 6,093,186 A | 7/2000 | Goble |
| 6,102,497 A | 8/2000 | Ehr et al. |
| 6,102,907 A | 8/2000 | Smethers et al. |
| 6,104,248 A | 8/2000 | Carver |
| 6,106,524 A | 8/2000 | Eggers et al. |
| 6,113,591 A | 9/2000 | Whayne et al. |
| 6,113,592 A | 9/2000 | Taylor |
| 6,113,593 A | 9/2000 | Tu et al. |

| Patent | Type | Date | Name |
|---|---|---|---|
| 6,113,596 | A | 9/2000 | Hooven |
| 6,123,701 | A | 9/2000 | Nezhat |
| 6,123,702 | A | 9/2000 | Swanson et al. |
| 6,132,429 | A | 10/2000 | Baker |
| 6,139,349 | A | 10/2000 | Wright |
| 6,142,992 | A | 11/2000 | Cheng et al. |
| 6,155,975 | A | 12/2000 | Urich et al. |
| 6,162,184 | A | 12/2000 | Swanson et al. |
| 6,162,217 | A | 12/2000 | Kannenberg et al. |
| 6,165,169 | A | 12/2000 | Panescu et al. |
| 6,165,173 | A | 12/2000 | Kamdar et al. |
| 6,171,304 | B1 | 1/2001 | Netherly et al. |
| 6,183,468 | B1 | 2/2001 | Swanson et al. |
| 6,186,147 | B1 * | 2/2001 | Cobb ............................ 128/898 |
| 6,188,211 | B1 | 2/2001 | Rincon-Mora et al. |
| 6,193,713 | B1 | 2/2001 | Geistert et al. |
| 6,197,023 | B1 | 3/2001 | Muntermann |
| 6,200,314 | B1 | 3/2001 | Sherman |
| 6,203,541 | B1 | 3/2001 | Keppel |
| 6,210,403 | B1 | 4/2001 | Klicek |
| 6,216,704 | B1 | 4/2001 | Ingle et al. |
| 6,222,356 | B1 | 4/2001 | Taghizadeh-Kaschani |
| 6,228,078 | B1 | 5/2001 | Eggers et al. |
| 6,228,080 | B1 | 5/2001 | Gines |
| 6,228,081 | B1 | 5/2001 | Goble |
| 6,231,569 | B1 | 5/2001 | Bek |
| 6,232,556 | B1 | 5/2001 | Daugherty et al. |
| 6,235,020 | B1 | 5/2001 | Cheng et al. |
| 6,235,022 | B1 | 5/2001 | Hallock et al. |
| 6,237,604 | B1 | 5/2001 | Burnside et al. |
| 6,238,387 | B1 | 5/2001 | Miller, III |
| 6,238,388 | B1 | 5/2001 | Ellman |
| 6,241,723 | B1 | 6/2001 | Heim et al. |
| 6,241,725 | B1 | 6/2001 | Cosman |
| 6,243,654 | B1 | 6/2001 | Johnson et al. |
| 6,245,061 | B1 | 6/2001 | Panescu et al. |
| 6,245,063 | B1 | 6/2001 | Uphoff |
| 6,245,065 | B1 | 6/2001 | Panescu |
| 6,246,912 | B1 | 6/2001 | Sluijter et al. |
| 6,251,106 | B1 | 6/2001 | Becker et al. |
| 6,254,422 | B1 | 7/2001 | Feye-Hohmann |
| 6,258,085 | B1 | 7/2001 | Eggleston |
| 6,259,937 | B1 | 7/2001 | Schulman et al. |
| 6,261,285 | B1 | 7/2001 | Novak |
| 6,261,286 | B1 | 7/2001 | Goble et al. |
| 6,267,760 | B1 | 7/2001 | Swanson |
| 6,270,497 | B1 | 8/2001 | Sekino et al. |
| 6,273,886 | B1 | 8/2001 | Edwards |
| 6,275,786 | B1 | 8/2001 | Daners |
| 6,287,304 | B1 | 9/2001 | Eggers et al. |
| 6,293,941 | B1 | 9/2001 | Strul |
| 6,293,942 | B1 | 9/2001 | Goble et al. |
| 6,293,943 | B1 | 9/2001 | Panescu et al. |
| 6,296,636 | B1 | 10/2001 | Cheng et al. |
| 6,304,138 | B1 | 10/2001 | Johnson |
| 6,306,131 | B1 | 10/2001 | Hareyama et al. |
| 6,306,134 | B1 | 10/2001 | Goble et al. |
| 6,309,386 | B1 | 10/2001 | Bek |
| 6,322,558 | B1 | 11/2001 | Taylor et al. |
| 6,325,799 | B1 | 12/2001 | Goble |
| 6,329,778 | B1 | 12/2001 | Culp et al. |
| 6,337,998 | B1 | 1/2002 | Behl et al. |
| 6,338,657 | B1 | 1/2002 | Harper et al. |
| 6,341,981 | B1 | 1/2002 | Gorman |
| 6,350,262 | B1 | 2/2002 | Ashley |
| 6,358,245 | B1 | 3/2002 | Edwards |
| 6,364,877 | B1 | 4/2002 | Goble et al. |
| 6,370,408 | B1 | 4/2002 | Merchant et al. |
| 6,371,963 | B1 | 4/2002 | Nishtala et al. |
| 6,383,183 | B1 | 5/2002 | Sekino et al. |
| 6,387,092 | B1 | 5/2002 | Burnside et al. |
| 6,391,024 | B1 | 5/2002 | Sun et al. |
| 6,398,779 | B1 | 6/2002 | Buysse et al. |
| 6,398,781 | B1 | 6/2002 | Goble et al. |
| 6,402,741 | B1 | 6/2002 | Keppel et al. |
| 6,402,742 | B1 | 6/2002 | Blewett et al. |
| 6,402,743 | B1 | 6/2002 | Orszulak et al. |
| 6,402,748 | B1 | 6/2002 | Schoenman et al. |
| 6,409,722 | B1 | 6/2002 | Hoey et al. |
| 6,413,256 | B1 | 7/2002 | Truckai et al. |
| 6,416,509 | B1 | 7/2002 | Goble et al. |
| 6,422,896 | B2 | 7/2002 | Aoki et al. |
| 6,423,057 | B1 | 7/2002 | He et al. |
| 6,424,186 | B1 | 7/2002 | Quimby et al. |
| 6,426,886 | B1 | 7/2002 | Goder |
| 6,428,537 | B1 | 8/2002 | Swanson et al. |
| 6,436,096 | B1 | 8/2002 | Hareyama |
| 6,440,157 | B1 | 8/2002 | Shigezawa et al. |
| 6,451,015 | B1 | 9/2002 | Rittman, III et al. |
| 6,454,594 | B2 | 9/2002 | Sawayanagi |
| 6,458,121 | B1 | 10/2002 | Rosenstock |
| 6,458,122 | B1 | 10/2002 | Pozzato |
| 6,464,689 | B1 | 10/2002 | Qin |
| 6,464,696 | B1 | 10/2002 | Oyama |
| 6,468,270 | B1 | 10/2002 | Hovda et al. |
| 6,468,273 | B1 | 10/2002 | Leveen et al. |
| 6,469,481 | B1 | 10/2002 | Tateishi |
| 6,482,201 | B1 | 11/2002 | Olsen et al. |
| 6,488,678 | B2 | 12/2002 | Sherman |
| 6,494,880 | B1 | 12/2002 | Swanson et al. |
| 6,497,659 | B1 | 12/2002 | Rafert |
| 6,498,466 | B1 | 12/2002 | Edwards |
| 6,506,189 | B1 | 1/2003 | Rittman, III et al. |
| 6,508,815 | B1 | 1/2003 | Strul |
| 6,511,476 | B2 | 1/2003 | Hareyama |
| 6,511,478 | B1 | 1/2003 | Burnside |
| 6,517,538 | B1 | 2/2003 | Jacob et al. |
| 6,522,931 | B2 | 2/2003 | Manker et al. |
| 6,524,308 | B1 | 2/2003 | Muller et al. |
| 6,537,272 | B2 | 3/2003 | Christopherson et al. |
| 6,544,258 | B2 | 4/2003 | Fleenor et al. |
| 6,544,260 | B1 | 4/2003 | Markel et al. |
| 6,546,270 | B1 | 4/2003 | Goldin et al. |
| 6,547,786 | B1 | 4/2003 | Goble |
| 6,557,559 | B1 | 5/2003 | Eggers et al. |
| 6,558,376 | B2 | 5/2003 | Bishop |
| 6,558,377 | B2 | 5/2003 | Lee et al. |
| 6,560,470 | B1 | 5/2003 | Pologe |
| 6,562,037 | B2 | 5/2003 | Paton |
| 6,565,559 | B2 | 5/2003 | Eggleston |
| 6,565,562 | B1 | 5/2003 | Shah et al. |
| 6,575,969 | B1 | 6/2003 | Rittman, III et al. |
| 6,578,579 | B2 | 6/2003 | Burnside et al. |
| 6,579,288 | B1 | 6/2003 | Swanson et al. |
| 6,582,427 | B1 | 6/2003 | Goble et al. |
| 6,602,243 | B2 | 8/2003 | Noda |
| 6,602,252 | B2 | 8/2003 | Mollenauer |
| 6,611,793 | B1 | 8/2003 | Burnside et al. |
| 6,620,157 | B1 | 9/2003 | Dabney et al. |
| 6,620,189 | B1 | 9/2003 | Sakurai et al. |
| 6,623,423 | B2 | 9/2003 | Machold et al. |
| 6,626,901 | B1 | 9/2003 | Treat et al. |
| 6,629,973 | B1 | 10/2003 | Wardell et al. |
| 6,629,974 | B2 | 10/2003 | Penny et al. |
| 6,632,193 | B1 | 10/2003 | Davison et al. |
| 6,635,056 | B2 | 10/2003 | Kadhiresan et al. |
| 6,635,057 | B2 | 10/2003 | Harano |
| 6,645,198 | B1 | 11/2003 | Bommannan et al. |
| 6,648,883 | B2 | 11/2003 | Francischelli |
| 6,651,669 | B1 | 11/2003 | Burnside |
| 6,652,513 | B2 | 11/2003 | Panescu et al. |
| 6,652,514 | B2 | 11/2003 | Ellman |
| 6,653,569 | B1 | 11/2003 | Sung |
| 6,656,177 | B2 | 12/2003 | Truckai et al. |
| 6,663,623 | B1 | 12/2003 | Oyama et al. |
| 6,663,624 | B2 | 12/2003 | Edwards et al. |
| 6,663,627 | B2 | 12/2003 | Francischelli et al. |
| 6,666,860 | B1 | 12/2003 | Takahashi |
| 6,672,151 | B1 | 1/2004 | Schultz et al. |
| 6,679,875 | B2 | 1/2004 | Honda |
| 6,682,527 | B2 | 1/2004 | Strul |
| 6,685,700 | B2 | 2/2004 | Behl |
| 6,685,701 | B2 | 2/2004 | Orszulak et al. |
| 6,685,703 | B2 | 2/2004 | Pearson et al. |
| 6,689,131 | B2 | 2/2004 | McClurken |
| 6,692,489 | B1 | 2/2004 | Heim |
| 6,693,782 | B1 | 2/2004 | Lash |
| 6,695,837 | B2 | 2/2004 | Howell |

| | | | |
|---|---|---|---|
| 6,696,844 B2 | 2/2004 | Wong et al. | |
| 6,712,813 B2 | 3/2004 | Ellman | |
| 6,723,091 B2 | 4/2004 | Goble et al. | |
| 6,730,078 B2 | 5/2004 | Simpson et al. | |
| 6,730,079 B2 | 5/2004 | Lovewell | |
| 6,730,080 B2 | 5/2004 | Harano | |
| 6,733,495 B1 | 5/2004 | Bek | |
| 6,733,498 B2 | 5/2004 | Paton | |
| 6,740,079 B1 | 5/2004 | Eggers | |
| 6,740,085 B2 | 5/2004 | Hareyama | |
| 6,743,225 B2 | 6/2004 | Sanchez et al. | |
| 6,746,284 B1 | 6/2004 | Spink, Jr. | |
| 6,749,624 B2 | 6/2004 | Knowlton | |
| 6,755,825 B2 | 6/2004 | Shoenman et al. | |
| 6,758,846 B2 | 7/2004 | Goble et al. | |
| 6,761,716 B2 | 7/2004 | Kadhiresan et al. | |
| 6,775,575 B2 | 8/2004 | Bommannan et al. | |
| 6,778,044 B2 | 8/2004 | Fehrenbach et al. | |
| 6,783,523 B2 | 8/2004 | Qin | |
| 6,784,405 B2 | 8/2004 | Flugstad et al. | |
| 6,786,905 B2 | 9/2004 | Swanson et al. | |
| 6,788,977 B2 | 9/2004 | Fenn et al. | |
| 6,790,206 B2 | 9/2004 | Panescu | |
| 6,792,390 B1 | 9/2004 | Burnside et al. | |
| 6,796,980 B2 | 9/2004 | Hall | |
| 6,796,981 B2 | 9/2004 | Wham et al. | |
| 6,809,508 B2 | 10/2004 | Donofrio | |
| 6,818,000 B2 | 11/2004 | Muller et al. | |
| 6,819,027 B2 | 11/2004 | Saraf | |
| 6,824,539 B2 | 11/2004 | Novak | |
| 6,830,569 B2 | 12/2004 | Thompson | |
| 6,837,888 B2 | 1/2005 | Ciarrocca et al. | |
| 6,843,682 B2 | 1/2005 | Matsuda et al. | |
| 6,843,789 B2 | 1/2005 | Goble | |
| 6,849,073 B2 | 2/2005 | Hoey | |
| 6,855,141 B2 | 2/2005 | Lovewell | |
| 6,855,142 B2 | 2/2005 | Harano | |
| 6,860,881 B2 | 3/2005 | Sturm | |
| 6,864,686 B2 | 3/2005 | Novak | |
| 6,875,210 B2 | 4/2005 | Refior | |
| 6,887,240 B1 | 5/2005 | Lands et al. | |
| 6,890,331 B2 | 5/2005 | Kristensen | |
| 6,893,435 B2 | 5/2005 | Goble | |
| 6,899,538 B2 | 5/2005 | Matoba | |
| 6,923,804 B2 | 8/2005 | Eggers et al. | |
| 6,929,641 B2 | 8/2005 | Goble et al. | |
| 6,936,047 B2 | 8/2005 | Nasab et al. | |
| 6,939,344 B2 | 9/2005 | Kreindel | |
| 6,939,346 B2 | 9/2005 | Kannenberg et al. | |
| 6,939,347 B2 | 9/2005 | Thompson | |
| 6,942,660 B2 | 9/2005 | Pantera et al. | |
| 6,948,503 B2 | 9/2005 | Refior et al. | |
| 6,953,461 B2 | 10/2005 | McClurken et al. | |
| 6,958,064 B2 | 10/2005 | Rioux et al. | |
| 6,962,587 B2 | 11/2005 | Johnson et al. | |
| 6,966,907 B2 | 11/2005 | Goble | |
| 6,970,752 B1 | 11/2005 | Lim et al. | |
| 6,974,453 B2 | 12/2005 | Woloszko et al. | |
| 6,974,463 B2 | 12/2005 | Magers et al. | |
| 6,977,495 B2 | 12/2005 | Donofrio | |
| 6,979,329 B2 | 12/2005 | Burnside et al. | |
| 6,984,231 B2 | 1/2006 | Goble et al. | |
| 6,989,010 B2 | 1/2006 | Francischelli et al. | |
| 6,994,704 B2 | 2/2006 | Qin et al. | |
| 6,994,707 B2 | 2/2006 | Ellman et al. | |
| 7,001,379 B2 | 2/2006 | Behl et al. | |
| 7,001,381 B2 | 2/2006 | Harano et al. | |
| 7,004,174 B2 | 2/2006 | Eggers et al. | |
| 7,008,369 B2 | 3/2006 | Cuppen | |
| 7,008,417 B2 | 3/2006 | Eick | |
| 7,008,421 B2 | 3/2006 | Daniel et al. | |
| 7,025,764 B2 | 4/2006 | Paton et al. | |
| 7,033,351 B2 | 4/2006 | Howell | |
| 7,041,096 B2 | 5/2006 | Malis et al. | |
| 7,044,948 B2 | 5/2006 | Keppel | |
| 7,044,949 B2 | 5/2006 | Orszulak et al. | |
| 7,048,687 B1 | 5/2006 | Reuss et al. | |
| 7,058,372 B1 | 6/2006 | Pardoen et al. | |
| 7,060,063 B2 | 6/2006 | Marion et al. | |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,087,054 B2 | 8/2006 | Truckai et al. |
| 7,094,231 B1 | 8/2006 | Ellman et al. |
| 7,104,834 B2 | 9/2006 | Robinson et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,842 B2 | 1/2007 | Sartor et al. |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,166,986 B2 | 1/2007 | Kendall |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,184,820 B2 | 2/2007 | Jersey-Willuhn et al. |
| 7,190,933 B2 | 3/2007 | DeRuijter et al. |
| 7,192,427 B2 | 3/2007 | Chapelon et al. |
| 7,195,627 B2 | 3/2007 | Amoah et al. |
| 7,200,010 B2 | 4/2007 | Broman et al. |
| 7,203,556 B2 | 4/2007 | Daners |
| 7,204,835 B2 | 4/2007 | Latterell et al. |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,233,278 B2 | 6/2007 | Eriksson |
| 7,238,181 B2 | 7/2007 | Daners et al. |
| 7,238,183 B2 | 7/2007 | Kreindel |
| 7,241,296 B2 | 7/2007 | Buysse et al. |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,269,034 B2 | 9/2007 | Schlecht |
| 7,276,068 B2 | 10/2007 | Johnson et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | Van Zyl |
| 7,311,703 B2 | 12/2007 | Turovskiy et al. |
| 7,316,682 B2 | 1/2008 | Konesky |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |

| | | | | | | |
|---|---|---|---|---|---|---|
| 7,367,972 B2 | 5/2008 | Francischelli et al. | 8,187,262 B2 | 5/2012 | Orszulak | |
| RE40,388 E | 6/2008 | Gines | 8,202,271 B2 | 6/2012 | Orszulak | |
| 7,396,336 B2 | 7/2008 | Orszulak et al. | 8,211,100 B2 | 7/2012 | Podhajsky et al. | |
| 7,402,754 B2 | 7/2008 | Kirwan, Jr. et al. | 8,216,219 B2 | 7/2012 | Desinger et al. | |
| D574,323 S | 8/2008 | Waaler | 8,216,220 B2 | 7/2012 | Jensen et al. | |
| 7,407,502 B2 | 8/2008 | Strul et al. | 8,216,223 B2 | 7/2012 | Wham et al. | |
| 7,416,437 B2 | 8/2008 | Sartor et al. | 8,226,639 B2 | 7/2012 | Podhajsky et al. | |
| 7,416,549 B2 | 8/2008 | Young et al. | 8,231,553 B2 | 7/2012 | Joseph et al. | |
| 7,422,582 B2 | 9/2008 | Malackowski et al. | 8,231,616 B2 | 7/2012 | McPherson et al. | |
| 7,422,586 B2 | 9/2008 | Morris et al. | 8,235,917 B2 | 8/2012 | Joseph et al. | |
| 7,425,835 B2 | 9/2008 | Eisele | 8,241,278 B2 | 8/2012 | Sartor | |
| 7,465,302 B2 | 12/2008 | Odell et al. | 8,242,782 B2 | 8/2012 | Brannan et al. | |
| 7,470,272 B2 | 12/2008 | Mulier et al. | 8,248,075 B2 | 8/2012 | Brannan et al. | |
| 7,477,080 B1 | 1/2009 | Fest | 8,257,349 B2 | 9/2012 | Orszulak | |
| 7,479,140 B2 | 1/2009 | Ellman et al. | 8,262,652 B2 | 9/2012 | Podhajsky | |
| 7,491,199 B2 | 2/2009 | Goble | 2002/0029036 A1 | 3/2002 | Goble et al. | |
| 7,491,201 B2 | 2/2009 | Shields et al. | 2002/0068931 A1* | 6/2002 | Wong et al. | 606/34 |
| 7,503,917 B2 | 3/2009 | Sartor et al. | 2003/0153908 A1 | 8/2003 | Goble et al. | |
| 7,511,472 B1 | 3/2009 | Xia et al. | 2003/0181898 A1 | 9/2003 | Bowers | |
| 7,513,896 B2 | 4/2009 | Orszulak | 2003/0229344 A1 | 12/2003 | Dycus et al. | |
| 7,517,351 B2 | 4/2009 | Culp et al. | 2004/0015159 A1 | 1/2004 | Slater et al. | |
| 7,525,398 B2 | 4/2009 | Nishimura et al. | 2004/0030330 A1 | 2/2004 | Brassell et al. | |
| 7,568,619 B2 | 8/2009 | Todd et al. | 2004/0068304 A1 | 4/2004 | Paton | |
| 7,573,693 B2 | 8/2009 | Hornung | 2004/0097912 A1 | 5/2004 | Gonnering | |
| 7,582,084 B2 | 9/2009 | Swanson et al. | 2004/0133189 A1 | 7/2004 | Sakurai | |
| 7,621,041 B2 | 11/2009 | Banerji et al. | 2004/0172016 A1 | 9/2004 | Bek et al. | |
| 7,628,786 B2 | 12/2009 | Plaven et al. | 2004/0193021 A1 | 9/2004 | Zdeblick et al. | |
| 7,648,499 B2 | 1/2010 | Orszulak et al. | 2005/0004634 A1 | 1/2005 | Ricart et al. | |
| 7,651,492 B2 | 1/2010 | Wham | 2005/0021020 A1 | 1/2005 | Blaha | |
| 7,651,493 B2 | 1/2010 | Arts et al. | 2005/0109111 A1 | 5/2005 | Manlove et al. | |
| 7,655,003 B2 | 2/2010 | Lorang et al. | 2005/0109935 A1 | 5/2005 | Manlove et al. | |
| 7,666,182 B2 | 2/2010 | Klett et al. | 2005/0131390 A1 | 6/2005 | Heinrich et al. | |
| 7,675,429 B2 | 3/2010 | Cernasov | 2006/0079774 A1 | 4/2006 | Anderson | |
| 7,678,105 B2 | 3/2010 | McGreevy et al. | 2006/0111711 A1 | 5/2006 | Goble | |
| 7,722,601 B2 | 5/2010 | Wham et al. | 2006/0155270 A1 | 7/2006 | Hancock et al. | |
| 7,731,717 B2 | 6/2010 | Odom et al. | 2006/0161148 A1 | 7/2006 | Behnke | |
| 7,736,358 B2 | 6/2010 | Shores et al. | 2006/0191926 A1 | 8/2006 | Ray et al. | |
| 7,744,593 B2 | 6/2010 | Mihori | 2006/0224053 A1 | 10/2006 | Black et al. | |
| 7,749,217 B2 | 7/2010 | Podhajsky | 2006/0224152 A1 | 10/2006 | Behnke et al. | |
| 7,766,693 B2 | 8/2010 | Sartor et al. | 2006/0291178 A1 | 12/2006 | Shih | |
| 7,766,905 B2 | 8/2010 | Paterson et al. | 2007/0088413 A1 | 4/2007 | Weber et al. | |
| 7,780,662 B2 | 8/2010 | Bahney | 2007/0093801 A1 | 4/2007 | Behnke | |
| 7,780,764 B2 | 8/2010 | Baksh | 2007/0173802 A1 | 7/2007 | Keppel | |
| 7,794,457 B2 | 9/2010 | McPherson et al. | 2007/0173803 A1 | 7/2007 | Wham et al. | |
| 7,799,020 B2 | 9/2010 | Shores et al. | 2007/0173805 A1 | 7/2007 | Weinberg et al. | |
| 7,799,026 B2 | 9/2010 | Schechter et al. | 2007/0173811 A1* | 7/2007 | Couture et al. | 606/39 |
| 7,824,400 B2 | 11/2010 | Keppel | 2007/0173813 A1 | 7/2007 | Odom | |
| 7,834,484 B2 | 11/2010 | Sartor | 2007/0203481 A1 | 8/2007 | Gregg et al. | |
| 7,863,841 B2 | 1/2011 | Menegoli et al. | 2007/0265612 A1 | 11/2007 | Behnke et al. | |
| 7,864,129 B2 | 1/2011 | Konishi | 2007/0282320 A1 | 12/2007 | Buysse et al. | |
| 7,879,033 B2 | 2/2011 | Sartor et al. | 2008/0004619 A1 | 1/2008 | Malis et al. | |
| 7,901,400 B2 | 3/2011 | Wham et al. | 2008/0015563 A1 | 1/2008 | Hoey et al. | |
| 7,927,328 B2 | 4/2011 | Orszulak et al. | 2008/0015570 A1 | 1/2008 | Ormsby et al. | |
| 7,947,039 B2 | 5/2011 | Sartor | 2008/0071257 A1 | 3/2008 | Kotmel et al. | |
| 7,956,620 B2 | 6/2011 | Gilbert | 2008/0071260 A1 | 3/2008 | Shores | |
| 7,959,626 B2 | 6/2011 | Hong et al. | 2008/0132893 A1 | 6/2008 | D'Amelio et al. | |
| 7,972,328 B2 | 7/2011 | Wham et al. | 2008/0177199 A1 | 7/2008 | Podhajsky | |
| 7,972,332 B2 | 7/2011 | Arts et al. | 2008/0203997 A1 | 8/2008 | Foran et al. | |
| 7,976,544 B2 | 7/2011 | McClurken et al. | 2008/0234574 A1 | 9/2008 | Hancock et al. | |
| 8,004,121 B2 | 8/2011 | Sartor | 2008/0262489 A1* | 10/2008 | Steinke | 606/33 |
| 8,012,150 B2 | 9/2011 | Wham et al. | 2008/0281311 A1 | 11/2008 | Dunning et al. | |
| 8,025,660 B2 | 9/2011 | Plaven et al. | 2008/0281315 A1 | 11/2008 | Gines | |
| 8,034,049 B2 | 10/2011 | Odom et al. | 2008/0281316 A1 | 11/2008 | Carlton et al. | |
| 8,038,676 B2 | 10/2011 | Fischer | 2008/0287943 A1 | 11/2008 | Weber et al. | |
| 8,080,008 B2 | 12/2011 | Wham et al. | 2009/0018536 A1 | 1/2009 | Behnke | |
| 8,083,735 B2 | 12/2011 | Morris | 2009/0082765 A1 | 3/2009 | Collins et al. | |
| 8,096,961 B2 | 1/2012 | Orszulak et al. | 2009/0146635 A1 | 6/2009 | Qiu et al. | |
| 8,104,596 B2 | 1/2012 | Kim et al. | 2009/0157071 A1 | 6/2009 | Wham et al. | |
| 8,105,323 B2 | 1/2012 | Buysse et al. | 2009/0234350 A1 | 9/2009 | Behnke et al. | |
| 8,113,057 B2 | 2/2012 | Orszulak et al. | 2009/0240244 A1 | 9/2009 | Malis et al. | |
| 8,133,218 B2 | 3/2012 | Daw et al. | 2009/0248003 A1 | 10/2009 | Orszulak | |
| 8,133,222 B2 | 3/2012 | Ormsby | 2009/0248006 A1 | 10/2009 | Paulus et al. | |
| 8,147,485 B2 | 4/2012 | Wham et al. | 2009/0248007 A1 | 10/2009 | Falkenstein et al. | |
| 8,152,800 B2 | 4/2012 | Behnke | 2009/0254077 A1 | 10/2009 | Craig | |
| 8,152,801 B2 | 4/2012 | Goldberg et al. | 2009/0259224 A1 | 10/2009 | Wham et al. | |
| 8,152,802 B2 | 4/2012 | Podhajsky et al. | 2009/0292283 A1 | 11/2009 | Odom | |
| 8,162,932 B2 | 4/2012 | Podhajsky et al. | 2010/0030210 A1 | 2/2010 | Paulus | |
| 8,167,875 B2 | 5/2012 | Podhajsky et al. | 2010/0042093 A9 | 2/2010 | Wham et al. | |
| 8,174,267 B2 | 5/2012 | Brannan et al. | 2010/0057076 A1 | 3/2010 | Behnke et al. | |

| Publication No. | Date | Name |
|---|---|---|
| 2010/0063494 A1 | 3/2010 | Orszulak |
| 2010/0063497 A1 | 3/2010 | Orszulak |
| 2010/0076424 A1 | 3/2010 | Carr |
| 2010/0082022 A1 | 4/2010 | Haley et al. |
| 2010/0082023 A1 | 4/2010 | Brannan et al. |
| 2010/0082083 A1 | 4/2010 | Brannan et al. |
| 2010/0082084 A1 | 4/2010 | Brannan et al. |
| 2010/0094271 A1 | 4/2010 | Ward et al. |
| 2010/0094275 A1 | 4/2010 | Wham |
| 2010/0094288 A1 | 4/2010 | Kerr |
| 2010/0114090 A1 | 5/2010 | Hosier |
| 2010/0168730 A1 | 7/2010 | Hancock et al. |
| 2010/0168741 A1 | 7/2010 | Sanai et al. |
| 2010/0179533 A1 | 7/2010 | Podhajsky |
| 2010/0191233 A1 | 7/2010 | Wham et al. |
| 2010/0211063 A1 | 8/2010 | Wham et al. |
| 2010/0217258 A1 | 8/2010 | Floume et al. |
| 2010/0217264 A1 | 8/2010 | Odom et al. |
| 2010/0318080 A1 | 12/2010 | Keppel |
| 2011/0028963 A1 | 2/2011 | Gilbert |
| 2011/0054460 A1 | 3/2011 | Gilbert |
| 2011/0060329 A1 | 3/2011 | Gilbert |
| 2011/0071516 A1 | 3/2011 | Gregg |
| 2011/0071521 A1 | 3/2011 | Gilbert |
| 2011/0077631 A1 | 3/2011 | Keller |
| 2011/0112530 A1 | 5/2011 | Keller |
| 2011/0115562 A1 | 5/2011 | Gilbert |
| 2011/0144635 A1 | 6/2011 | Harper et al. |
| 2011/0178516 A1 | 7/2011 | Orszulak et al. |
| 2011/0204903 A1 | 8/2011 | Gilbert |
| 2011/0208179 A1 | 8/2011 | Prakash et al. |
| 2011/0213354 A1 | 9/2011 | Smith |
| 2011/0213355 A1 | 9/2011 | Behnke, II |
| 2011/0301607 A1 | 12/2011 | Couture |
| 2011/0318948 A1 | 12/2011 | Plaven et al. |
| 2011/0319881 A1 | 12/2011 | Johnston |
| 2012/0004703 A1 | 1/2012 | Deborski et al. |
| 2012/0010610 A1 | 1/2012 | Keppel |
| 2012/0022521 A1 | 1/2012 | Odom et al. |
| 2012/0029515 A1 | 2/2012 | Couture |
| 2012/0089139 A1 | 4/2012 | Wham et al. |
| 2012/0101491 A1 | 4/2012 | Blaha |
| 2012/0116268 A1 | 5/2012 | Orszulak et al. |
| 2012/0130256 A1 | 5/2012 | Buysse et al. |
| 2012/0150170 A1 | 6/2012 | Buysse et al. |
| 2012/0172866 A1 | 7/2012 | Behnke, II |
| 2012/0179156 A1 | 7/2012 | Behnke, II |
| 2012/0220997 A1 | 8/2012 | Johnston |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| DE | 10 2008 058737 | 4/2010 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 569130 | 11/1993 |
| EP | 608609 | 8/1994 |
| EP | 640317 | 3/1995 |
| EP | 694291 | 1/1996 |
| EP | 617925 | 7/1996 |
| EP | 836868 | 4/1998 |
| EP | 878169 | 11/1998 |
| EP | 882955 | 12/1998 |
| EP | 1051948 | 11/2000 |
| EP | 1053720 | 11/2000 |
| EP | 1151725 | 11/2001 |
| EP | 1278007 | 1/2003 |
| EP | 1293171 | 3/2003 |
| EP | 1472984 | 11/2004 |
| EP | 1495712 | 1/2005 |
| EP | 1500378 | 1/2005 |
| EP | 1146827 | 3/2005 |
| EP | 1535581 | 6/2005 |
| EP | 870473 | 9/2005 |
| EP | 1609430 | 12/2005 |
| EP | 1366724 | 1/2006 |
| EP | 1707144 | 3/2006 |
| EP | 1645235 | 4/2006 |
| EP | 880220 | 6/2006 |
| EP | 1681026 | 7/2006 |
| EP | 1707143 | 10/2006 |
| EP | 1744354 | 1/2007 |
| EP | 1776929 | 4/2007 |
| EP | 1810628 | 7/2007 |
| EP | 1810630 | 7/2007 |
| EP | 1810631 | 7/2007 |
| EP | 1810632 | 7/2007 |
| EP | 1810633 | 7/2007 |
| EP | 1810634 | 7/2007 |
| EP | 1849425 | 10/2007 |
| EP | 1854423 | 11/2007 |
| EP | 1862137 | 12/2007 |
| EP | 2025297 | 5/2008 |
| EP | 1263181 | 9/2008 |
| EP | 1994904 | 11/2008 |
| EP | 2100566 | 9/2009 |
| EP | 2111812 | 10/2009 |
| EP | 2253286 | 11/2010 |
| EP | 1594392 | 6/2011 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 1290304 | 9/1972 |
| GB | 2154881 | 9/1985 |
| GB | 2164473 | 3/1986 |
| GB | 2214430 | 9/1989 |
| GB | 2331247 | 5/1999 |
| GB | 2358934 | 8/2001 |
| GB | 2434872 | 8/2007 |
| JP | 63 005876 | 1/1988 |
| JP | 2002-065690 | 3/2002 |
| SU | 166452 | 1/1965 |
| SU | 727201 | 4/1980 |
| WO | WO92/06642 | 4/1992 |
| WO | WO92/07622 | 5/1992 |
| WO | WO93/24066 | 12/1993 |
| WO | WO94/10922 | 5/1994 |
| WO | WO94/24949 | 11/1994 |
| WO | WO94/28809 | 12/1994 |
| WO | WO95/09577 | 4/1995 |

| | | |
|---|---|---|
| WO | WO95/18575 | 7/1995 |
| WO | WO95/19148 | 7/1995 |
| WO | WO95/25471 | 9/1995 |
| WO | WO95/25472 | 9/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39085 | 12/1996 |
| WO | WO96/39086 | 12/1996 |
| WO | WO96/39088 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/10763 | 3/1997 |
| WO | WO97/11648 | 4/1997 |
| WO | WO97/17029 | 5/1997 |
| WO | WO97/43971 | 11/1997 |
| WO | WO98/07378 | 2/1998 |
| WO | WO98/18395 | 5/1998 |
| WO | WO98/27880 | 7/1998 |
| WO | WO99/12607 | 3/1999 |
| WO | WO99/56647 | 11/1999 |
| WO | WO00/48672 | 8/2000 |
| WO | WO00/54683 | 9/2000 |
| WO | WO01/01847 | 1/2001 |
| WO | WO02/00129 | 1/2002 |
| WO | WO02/11634 | 2/2002 |
| WO | WO02/32333 | 4/2002 |
| WO | WO02/32335 | 4/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/047446 | 6/2003 |
| WO | WO03/090630 | 11/2003 |
| WO | WO03/090635 | 11/2003 |
| WO | WO03/092520 | 11/2003 |
| WO | WO2004/028385 | 4/2004 |
| WO | WO2004/098385 | 4/2004 |
| WO | WO2004/043240 | 5/2004 |
| WO | WO2004/047659 | 6/2004 |
| WO | WO2004/052182 | 6/2004 |
| WO | WO2004/073488 | 9/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO2005/060365 | 7/2005 |
| WO | WO2005/060849 | 7/2005 |
| WO | WO2005/115235 | 12/2005 |
| WO | WO2005/117735 | 12/2005 |
| WO | WO2006/050888 | 5/2006 |
| WO | WO2006/105121 | 10/2006 |
| WO | WO2007/055491 | 5/2007 |
| WO | WO2007/067522 | 6/2007 |
| WO | WO2007/105963 | 9/2007 |
| WO | WO2008/002517 | 1/2008 |
| WO | WO2008/003058 | 1/2008 |
| WO | WO2008/011575 | 1/2008 |
| WO | WO2008/043999 | 4/2008 |
| WO | WO2008/044000 | 4/2008 |
| WO | WO2008/044013 | 4/2008 |
| WO | WO2008/053532 | 5/2008 |
| WO | WO2008/070562 | 6/2008 |
| WO | WO2008/071914 | 6/2008 |
| WO | WO2008/101356 | 8/2008 |
| WO | WO2008/110756 | 9/2008 |

OTHER PUBLICATIONS

U.S. Appl. No. 10/406,690, filed Apr. 3, 2003, Michael S. Klicek.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 13/048,639, filed Mar. 15, 2011, James S. Cunningham.
U.S. Appl. No. 13/049,459, filed Mar. 16, 2011, James H. Orszulak.
U.S. Appl. No. 13/050,770, filed Mar. 17, 2011, Robert B. Smith.
U.S. Appl. No. 13/085,258, filed Apr. 12, 2011, Ronald J. Podhajsky.
U.S. Appl. No. 13/085,278, filed Apr. 12, 2011, James A. Gilbert.
U.S. Appl. No. 13/118,973, filed May 31, 2011, James H. Orszulak.
U.S. Appl. No. 13/186,092, filed Jul. 19, 2011, George J. Collins.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.
U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/247,043, filed Sep. 28, 2011, Donald W. Heckel.
U.S. Appl. No. 13/358,129, filed Jan. 25, 2012, Joseph D. Brannan.
U.S. Appl. No. 13/360,140, filed Jan. 27, 2012, James E. Krapohl.
U.S. Appl. No. 13/426,204, filed Mar. 21, 2012, Robert B. Smith.
U.S. Appl. No. 13/427,111, filed Mar. 22, 2012, Daniel A. Joseph.
U.S. Appl. No. 13/442,460, filed Apr. 9, 2012, James E. Krapohl.
U.S. Appl. No. 13/446,096, filed Apr. 13, 2012, James H. Orszulak.
U.S. Appl. No. 13/469,960, filed May 11, 2012, Robert J. Behnke, II.
U.S. Appl. No. 13/483,815, filed May 30, 2012, Jeffrey R. Unger.
U.S. Appl. No. 13/485,083, filed May 31, 2012, Robert J. Behnke, II.
U.S. Appl. No. 13/526,205, filed Jun. 18, 2012, Jeffrey L. Jensen.
U.S. Appl. No. 13/540,347, filed Jul. 2, 2012, Ronald J. Podhajsky.
U.S. Appl. No. 13/593,550, filed Aug. 24, 2012, Ronald J. Podhajsky.
U.S. Appl. No. 13/584,192, filed Aug. 13, 2012, Joseph D. Brannan.
U.S. Appl. No. 13/587,400, filed Aug. 16, 2012, James H. Orszulak.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.

Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Zlatanovic M., "Sensors in Diffusion Plasma Processing" Microelectronics 1995; Proceedings 1995; $20^{th}$ International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400.9 dated Apr. 13, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP09763515.5 dated Nov. 29, 2011.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179305.7 dated Aug. 23, 2011.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11006233.8 dated Feb. 2, 2012.
International Search Report EP11155959.7 dated Jun. 30, 2011.
International Search Report EP11155960.5 dated Jun. 10, 2011.
International Search Report EP11168660 dated Sep. 28, 2011.
International Search Report EP11170959.8 dated Dec. 9, 2011.
International Search Report EP11173562.7 dated Nov. 24, 2011.
International Search Report EP11182150.0 dated Nov. 17, 2011.
International Search Report EP11188798.0 dated Dec. 27, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
US 6,878,148, 04/2005, Goble et al. (withdrawn)

* cited by examiner

IMAGINARY IMPEDANCE PROCESS MONITORING AND INTELLIGENT SHUT-OFF

CROSS-REFERENCE TO RELATED APPLICATION

The present application is a divisional of U.S. patent application Ser. No. 12/477,245 entitled "IMAGINARY IMPEDANCE PROCESS MONITORING AND INTELLIGENT SHUT-OFF" filed Jun. 3, 2009, which is a continuation-in-part of U.S. Pat. No. 8,167,875 entitled "ENERGY DELIVERY ALGORITHM FOR MEDICAL DEVICES," U.S. Pat. No. 8,152,802 entitled "ENERGY DELIVERY ALGORITHM FILTER PRE-LOADING," and U.S. Pat. No. 8,162,932 entitled "ENERGY DELIVERY ALGORITHM IMPEDANCE TREND ADAPTATION," all of which were filed on Jan. 12, 2009, the disclosures of each of which are hereby incorporated by reference herein in their entirety.

BACKGROUND

1. Technical Field

The present disclosure relates to electrosurgical apparatuses, systems and methods. More particularly, the present disclosure is directed to electrosurgical systems and methods for monitoring electrosurgical procedures and intelligent termination thereof based on imaginary impedance.

2. Background of Related Art

Energy-based tissue treatment is well known in the art. Various types of energy (e.g., electrical, ohmic, resistive, ultrasonic, microwave, cryogenic, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon that is applied to the tissue. A patient return electrode is placed remotely from the active electrode to carry the current back to the generator.

Ablation is most commonly a monopolar procedure that is particularly useful in the field of cancer treatment, where one or more RF ablation needle electrodes that (usually of elongated cylindrical geometry) are inserted into a living body. A typical form of such needle electrodes incorporates an insulated sheath disposed over an exposed (uninsulated) tip. When the RF energy is provided between the return electrode and the inserted ablation electrode, RF current flows from the needle electrode through the body. Typically, the current density is very high near the tip of the needle electrode, which tends to heat and destroy surrounding issue.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact with body tissue with either of the separated electrodes prevents the flow of current.

Bipolar electrosurgical techniques and instruments can be used to coagulate blood vessels or tissue, e.g., soft tissue structures, such as lung, brain and intestine. A surgeon can either cauterize, coagulate/desiccate and/or simply reduce or slow bleeding, by controlling the intensity, frequency and duration of the electrosurgical energy applied between the electrodes and through the tissue. In order to achieve one of these desired surgical effects without causing unwanted charring of tissue at the surgical site or causing collateral damage to adjacent tissue, e.g., thermal spread, it is necessary to control the output from the electrosurgical generator, e.g., power, waveform, voltage, current, pulse rate, etc.

It is known that measuring the electrical impedance and changes thereof across the tissue at the surgical site provides a good indication of the state of desiccation or drying of the tissue, e.g., as the tissue dries or loses moisture, the impedance across the tissue rises. This observation has been utilized in some electrosurgical generators to regulate the electrosurgical power based on measured tissue impedance.

SUMMARY

According to one embodiment of the present disclosure, an electrosurgical generator for supplying electrosurgical energy to tissue is disclosed. The generator includes sensor circuitry configured to measure an imaginary impedance and/or a rate of change of the imaginary impedance of tissue. The generator also includes a controller configured to regulate output of the electrosurgical generator based on the measured imaginary impedance and/or the rate of change of the imaginary impedance.

A method for supplying electrosurgical energy to tissue is also contemplated by the present disclosure. The method includes the steps of: measuring an imaginary impedance and/or a rate of change of the imaginary impedance of tissue and regulating output of the electrosurgical generator based on the measured imaginary impedance and/or the rate of change of the imaginary impedance.

Another method for supplying electrosurgical energy to tissue is also contemplated by the present disclosure. The method includes the steps of: measuring an imaginary impedance and/or a rate of change of the imaginary impedance of tissue and regulating output of the electrosurgical generator based on the measured imaginary impedance and/or the rate of change of the imaginary impedance and during the regulating step comparing the rate of change of the imaginary impedance with a first predetermined threshold and a second predetermined threshold.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The generator according to the present disclosure can perform monopolar and bipolar electrosurgical procedures as well as microwave ablation procedures, including vessel sealing procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

Figure 1A:
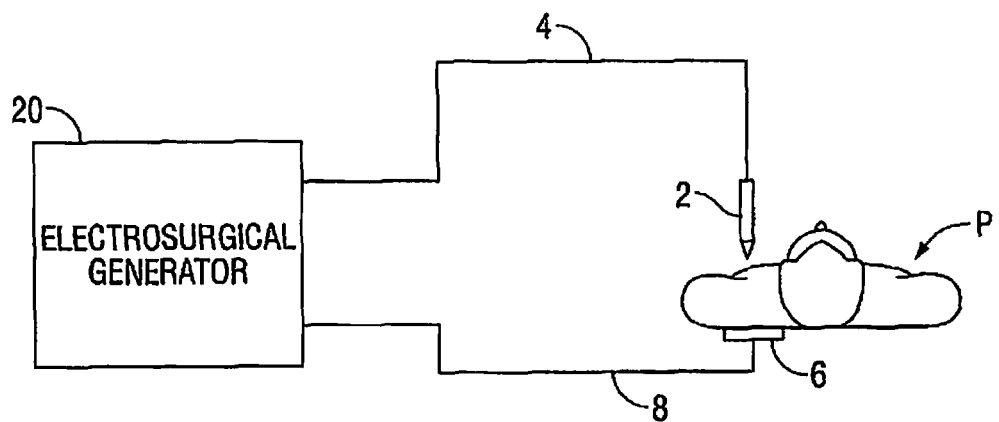
FIG. 1A is a schematic block diagram of a monopolar electrosurgical system according to one embodiment of the present disclosure.

FIG. 1A is a schematic illustration of a monopolar electrosurgical system according to one embodiment of the present disclosure. The system includes an electrosurgical instrument 2 having one or more electrodes for treating tissue of a patient P. The instrument 2 is a monopolar type instrument including one or more active electrodes (e.g., electrosurgical cutting probe, ablation electrode(s), etc.). Electrosurgical RF energy is supplied to the instrument 2 by a generator 20 via an supply line 4, which is connected to an active terminal 30 (FIG. 2) of the generator 20, allowing the instrument 2 to coagulate, seal, ablate and/or otherwise treat tissue. The energy is returned to the generator 20 through a return electrode 6 via a return line 8 at a return terminal 32 (FIG. 2) of the generator 20. The active terminal 30 and the return terminal 32 are connectors configured to interface with plugs (not explicitly shown) of the instrument 2 and the return electrode 6, which are disposed at the ends of the supply line 4 and the return line 8, respectively.

The system may include a plurality of return electrodes 6 that are arranged to minimize the chances of tissue damage by maximizing the overall contact area with the patient P. In addition, the generator 20 and the return electrode 6 may be configured for monitoring so-called "tissue-to-patient" contact to insure that sufficient contact exists therebetween to further minimize chances of tissue damage.

Figure 1B:
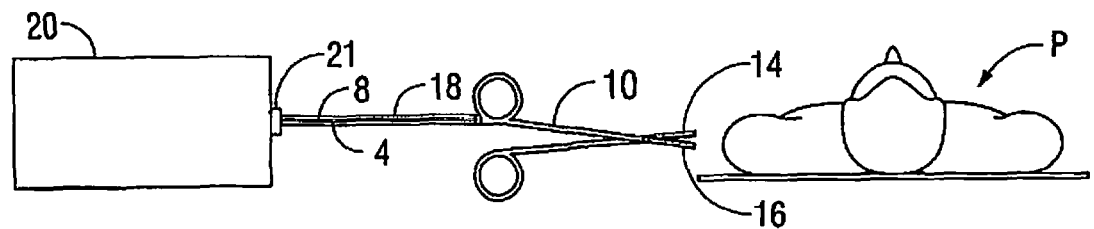
FIG. 1B is a schematic block diagram of a bipolar electrosurgical system according to one embodiment of the present disclosure.
Figure 2:
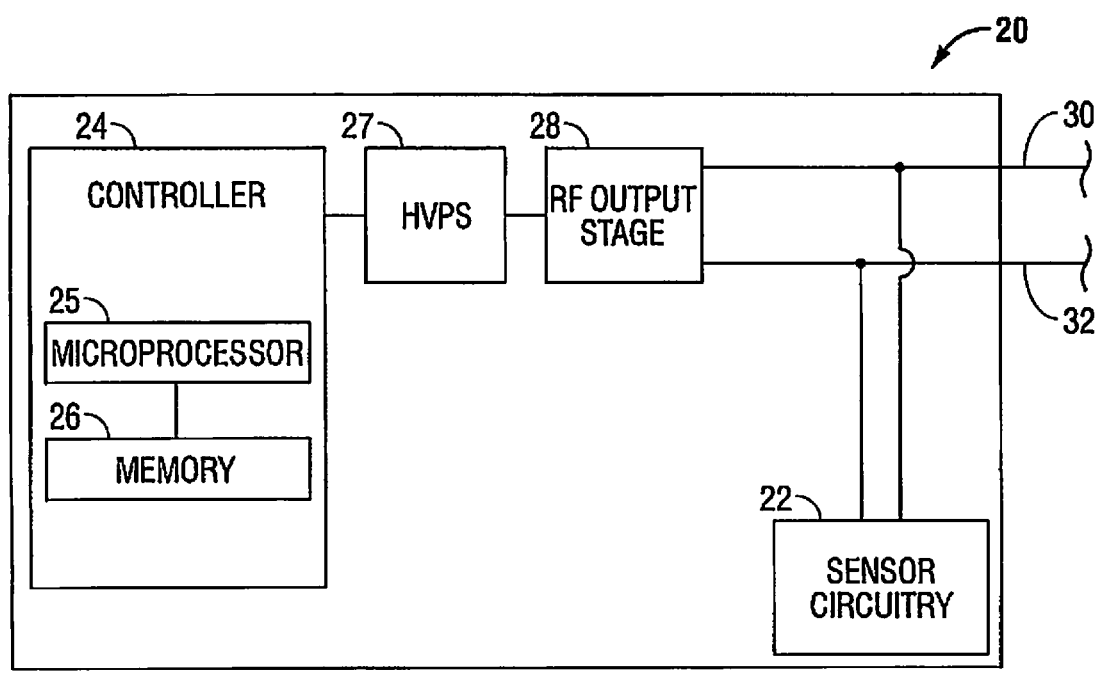
FIG. 2 is a schematic block diagram of a generator according to an embodiment of the present disclosure.

FIG. 1B is a schematic illustration of a bipolar electrosurgical system according to the present disclosure. The system includes a bipolar electrosurgical forceps 10 having one or more electrodes for treating tissue of a patient P. The electrosurgical forceps 10 includes opposing jaw members having an active electrode 14 and a return electrode 16 disposed therein. The active electrode 14 and the return electrode 16 are connected to the generator 20 through cable 18, which includes the supply and return lines 4, 8 coupled to the active and return terminals 30, 32, respectively (FIG. 2). The electrosurgical forceps 10 is coupled to the generator 20 at a connector 21 having connections to the active and return terminals 30 and 32 (e.g., pins) via a plug disposed at the end of the cable 18, wherein the plug includes contacts from the supply and return lines 4, 8.

The generator 20 includes suitable input controls (e.g., buttons, activators, switches, touch screen, etc.) for controlling the generator 20. In addition, the generator 20 may include one or more display screens for providing the user with variety of output information (e.g., intensity settings, treatment complete indicators, etc.). The controls allow the user to adjust power of the RF energy, waveform parameters (e.g., crest factor, duty cycle, etc.), and other parameters to achieve the desired waveform suitable for a particular task (e.g., coagulating, tissue sealing, intensity setting, etc.). The instrument 2 may also include a plurality of input controls that may be redundant with certain input controls of the generator 20. Placing the input controls at the instrument 2 allows for easier and faster modification of RF energy parameters during the surgical procedure without requiring interaction with the generator 20.

FIG. 2 shows a schematic block diagram of the generator 20 having a controller 24, a high voltage DC power supply 27 ("HVPS") and an RF output stage 28. The HVPS 27 is connected to a conventional AC source (e.g., electrical wall outlet) and provides high voltage DC power to an RF output stage 28, which then converts high voltage DC power into RF energy and delivers the RF energy to the active terminal 30. The energy is returned thereto via the return terminal 32.

In particular, the RF output stage 28 generates sinusoidal waveforms of high RF energy. The RF output stage 28 is configured to generate a plurality of waveforms having various duty cycles, peak voltages, crest factors, and other suitable parameters. Certain types of waveforms are suitable for specific electrosurgical modes. For instance, the RF output stage 28 generates a 100% duty cycle sinusoidal waveform in cut mode, which is best suited for ablating, fusing and dissecting tissue and a 1-25% duty cycle waveform in coagulation mode, which is best used for cauterizing tissue to stop bleeding.

The generator 20 may include a plurality of connectors to accommodate various types of electrosurgical instruments (e.g., instrument 2, electrosurgical forceps 10, etc.). Further, the generator 20 is configured to operate in a variety of modes such as ablation, monopolar and bipolar cutting coagulation, etc. It is envisioned that the generator 20 may include a switching mechanism (e.g., relays) to switch the supply of RF energy between the connectors, such that, for instance, when the instrument 2 is connected to the generator 20, only the monopolar plug receives RF energy.

The controller 24 includes a microprocessor 25 operably connected to a memory 26, which may be volatile type memory (e.g., RAM) and/or non-volatile type memory (e.g., flash media, disk media, etc.). The microprocessor 25 includes an output port that is operably connected to the HVPS 27 and/or RF output stage 28 allowing the microprocessor 25 to control the output of the generator 20 according to either open and/or closed control loop schemes. Those skilled in the art will appreciate that the microprocessor 25 may be substituted by any logic processor (e.g., control circuit) adapted to perform the calculations discussed herein.

A closed loop control scheme is a feedback control loop wherein sensor circuitry 22, which may include a plurality of sensors measuring a variety of tissue and energy properties (e.g., tissue impedance, tissue temperature, output current and/or voltage, voltage and current passing through the tissue, etc.), provides feedback to the controller 24. Such sensors are within the purview of those skilled in the art. The controller 24 then signals the HVPS 27 and/or RF output stage 28, which then adjust DC and/or RF power supply, respectively. The controller 24 also receives input signals from the input controls of the generator 20 or the instrument 2. The controller 24 utilizes the input signals to adjust power outputted by the generator 20 and/or performs other control functions thereon.

The present disclosure provides for a system and method for monitoring electrosurgical procedures using imaginary impedance. The use of imaginary impedance to control delivery of electrosurgical energy is discussed with respect to performing ablation procedures. Those skilled in the art will appreciate that the illustrated embodiments may be utilized with other electrosurgical procedures and/or modes.

Figure 3:
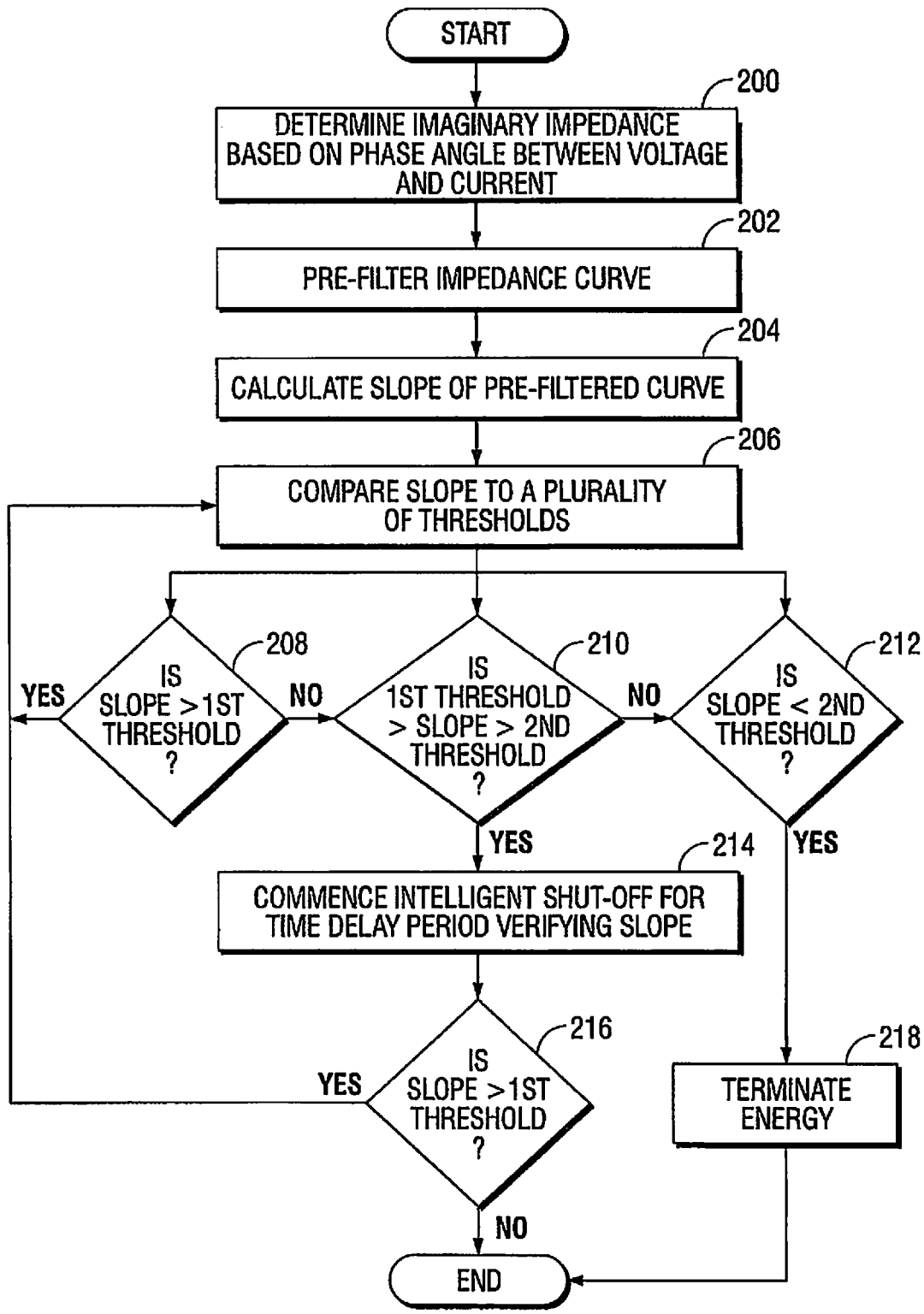
FIG. 3 is a flow chart of a method according to one embodiment of the present disclosure.

FIG. 3 shows a method for controlling output of the generator 20 based on imaginary impedance. The method may be embodied as a software application embedded in the memory 26 and executed by the microprocessor 25 to control generator 20 output based on measured imaginary impedance or changes in imaginary impedance as a function of time. Complex impedance consists of real and imaginary impedance. Real impedance is identified with resistance and imaginary impedance is identified with reactance. In addition, reactive impedance may be either inductive or capacitive. Purely resistive impedance exhibits no phase shift between the voltage and current, whereas reactance induces a phase shift θ between the voltage and the current passing through the tissue, thus imaginary impedance may be calculated based on the phase angle or phase shift between the voltage and current waveforms.

Changes in the imaginary impedance during energy delivery may be used as an indication of changes in tissue properties due to energy application. More specifically, imaginary impedance may be used to detect the formation of microbubbles, bubble fields and tissue desiccation that impart an electrical reactivity to the tissue that corresponds to sensed imaginary impedance. The tissue reactivity is reflective of the energy that is being delivered into the tissue. Thus, the measured change in imaginary impedance may be used as an indication of the amount of energy resident in the tissue. Monitoring of the resident energy in combination with monitoring of the energy being supplied by the generator allows for calculation of energy escaping the tissue during treatment, thereby allowing for determination of efficiency of the treatment process as well as any inadvertent energy drains.

Figure 4:
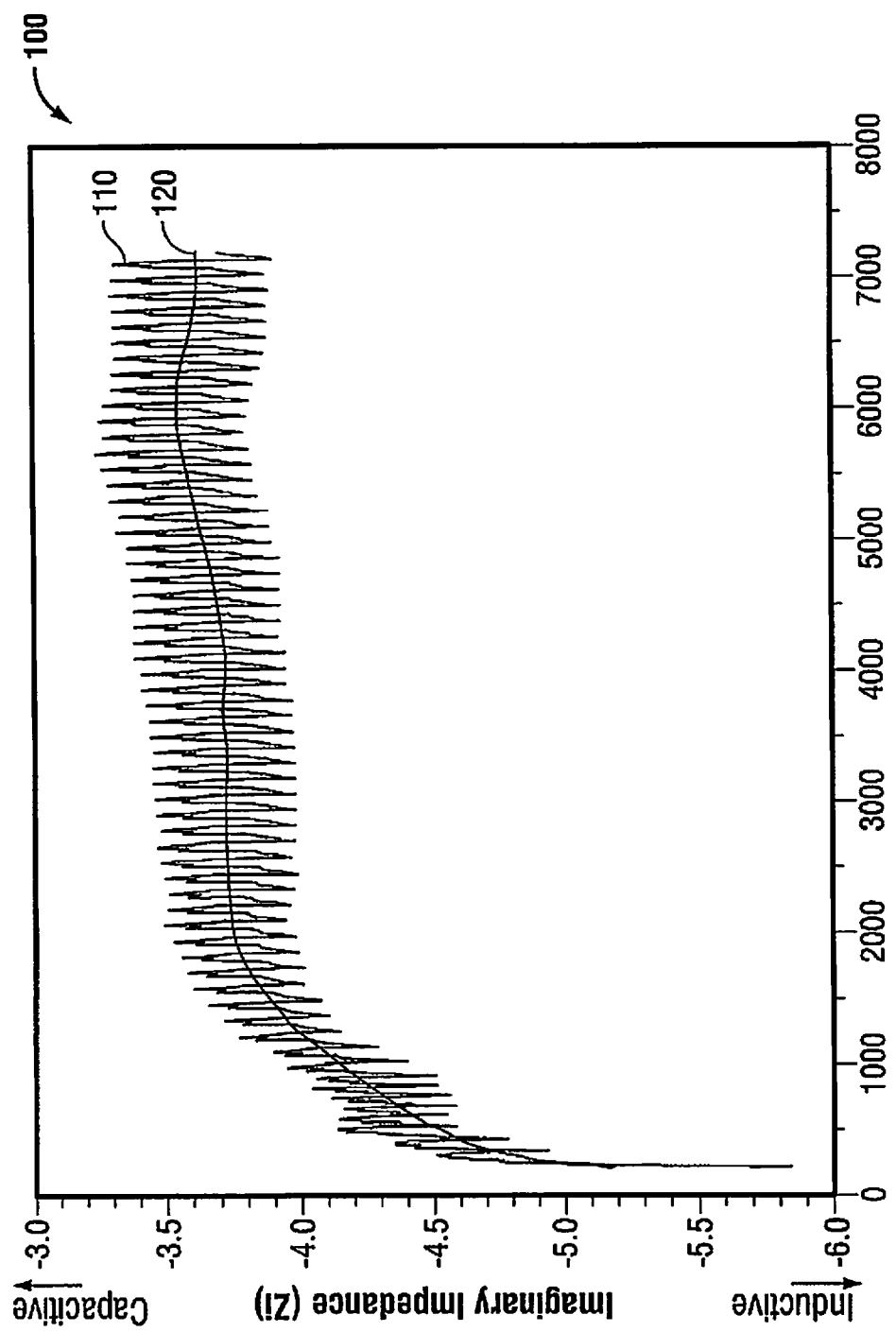
FIG. 4 is a plot of imaginary impedance of tissue during application of electrosurgical energy according to one embodiment of the present disclosure.

With reference to FIG. 3, in step 200, ablation energy is delivered into tissue and the imaginary impedance is measured by the sensor circuitry 22. The sensor circuitry 22 measures voltage and current waveforms passing through the tissue and determines the imaginary impedance (e.g., the imaginary component of the complex impedance) based on the phase angle between the waveforms. FIG. 4 illustrates a graph 100 of imaginary impedance vs. time (10 samples per second). The graph 100 includes detected impedance curve 110 having multiple pulses reflective of pulsatile application of electrosurgical energy. The impedance curve 110 is represented using negative numbers (e.g., −3Ω to −6Ω), such that higher negative numbers indicate greater reactive inductance and smaller negative numbers indicate more reactive capacitance. In step 202, the impedance curve 110 is pre-filtered to allow for faster processing to generate a pre-filtered curve 120. Various filters may be utilized to achieve the pre-filtered curve 120, such as Kalman Filter and the like.

Figure 5:
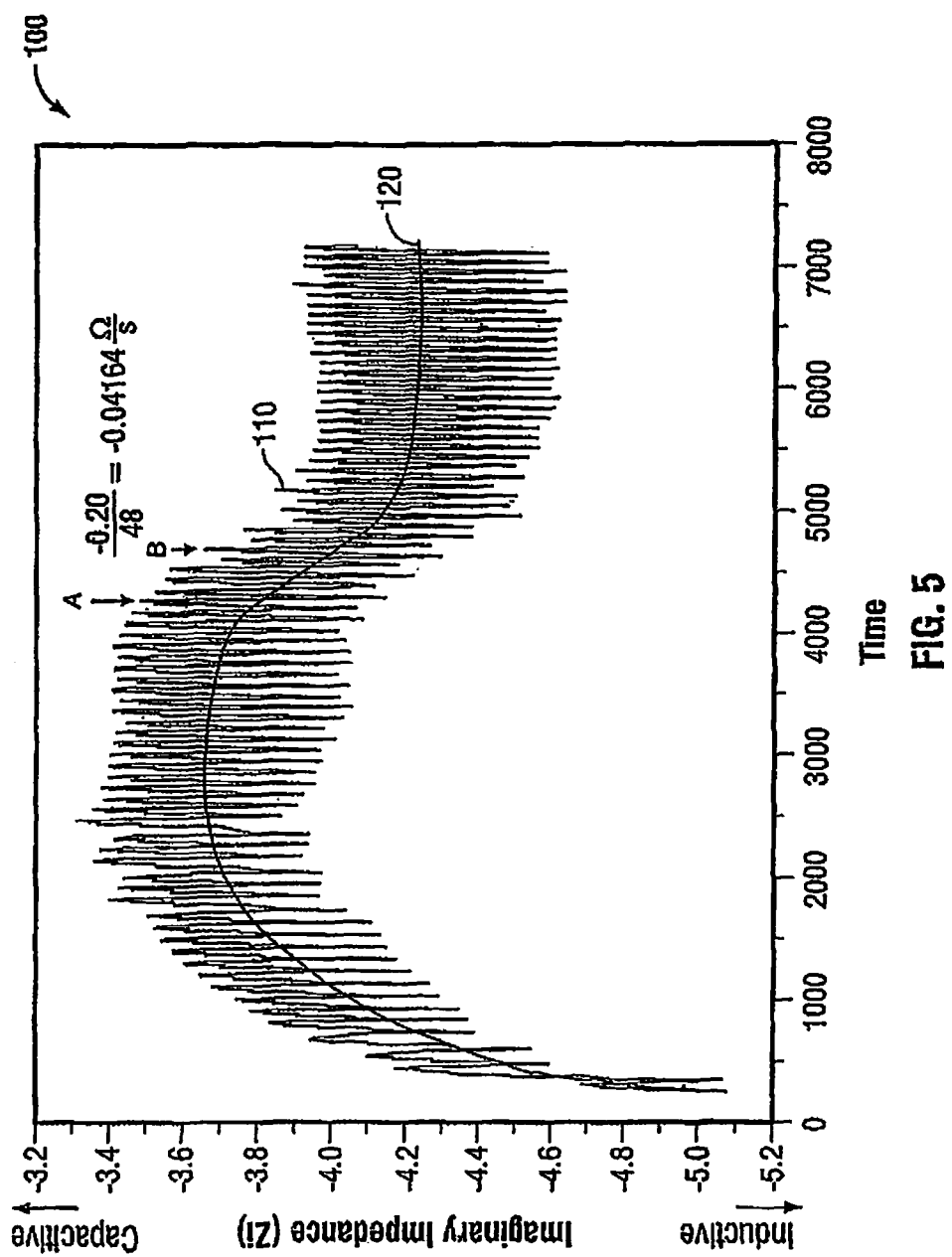
FIG. 5 is a plot of imaginary impedance of tissue during application of electrosurgical energy according to one embodiment of the present disclosure.
Figure 6:
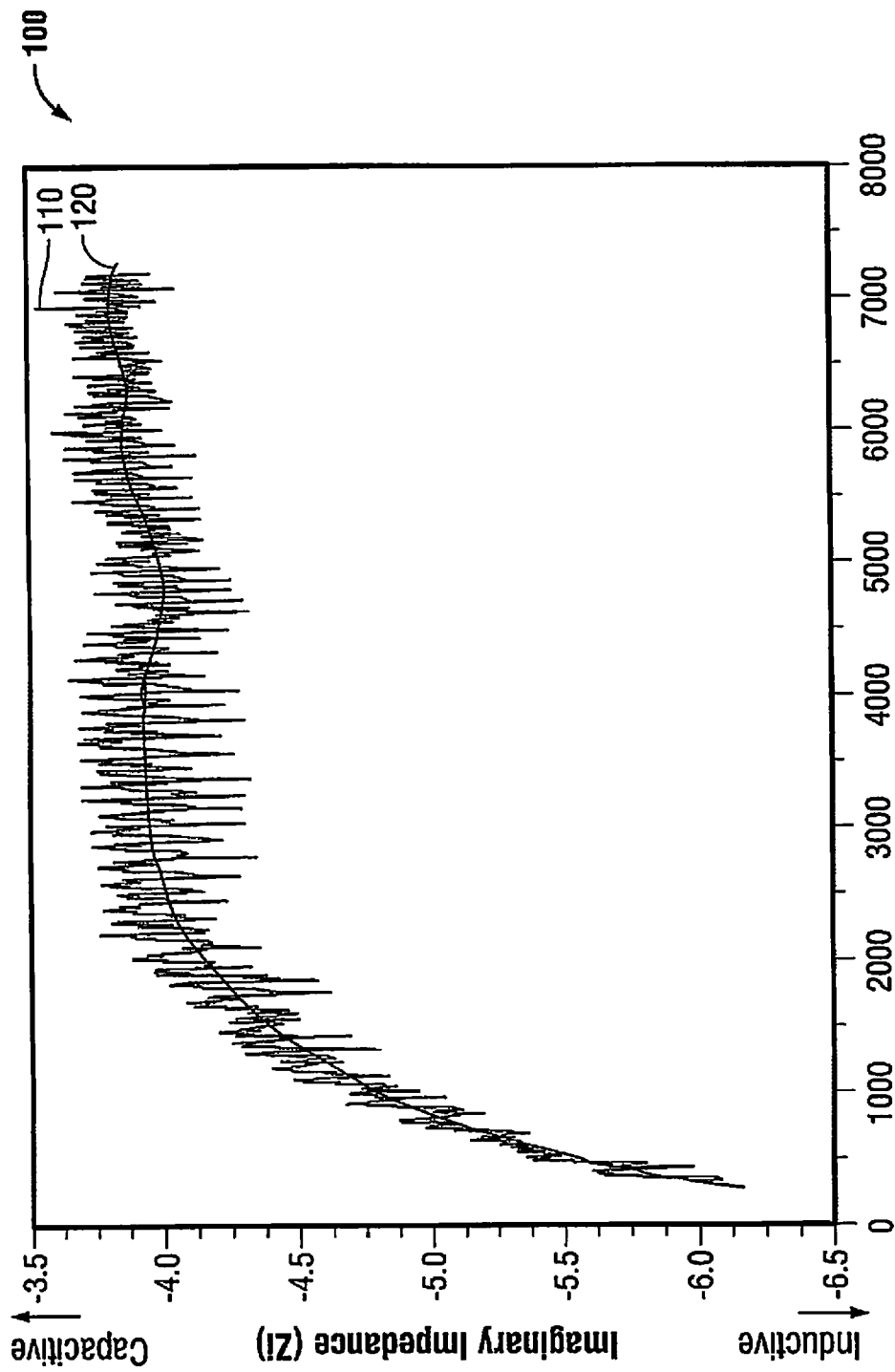
FIG. 6 is a plot of imaginary impedance of tissue during application of electrosurgical energy according to one embodiment of the present disclosure.
Figure 7:
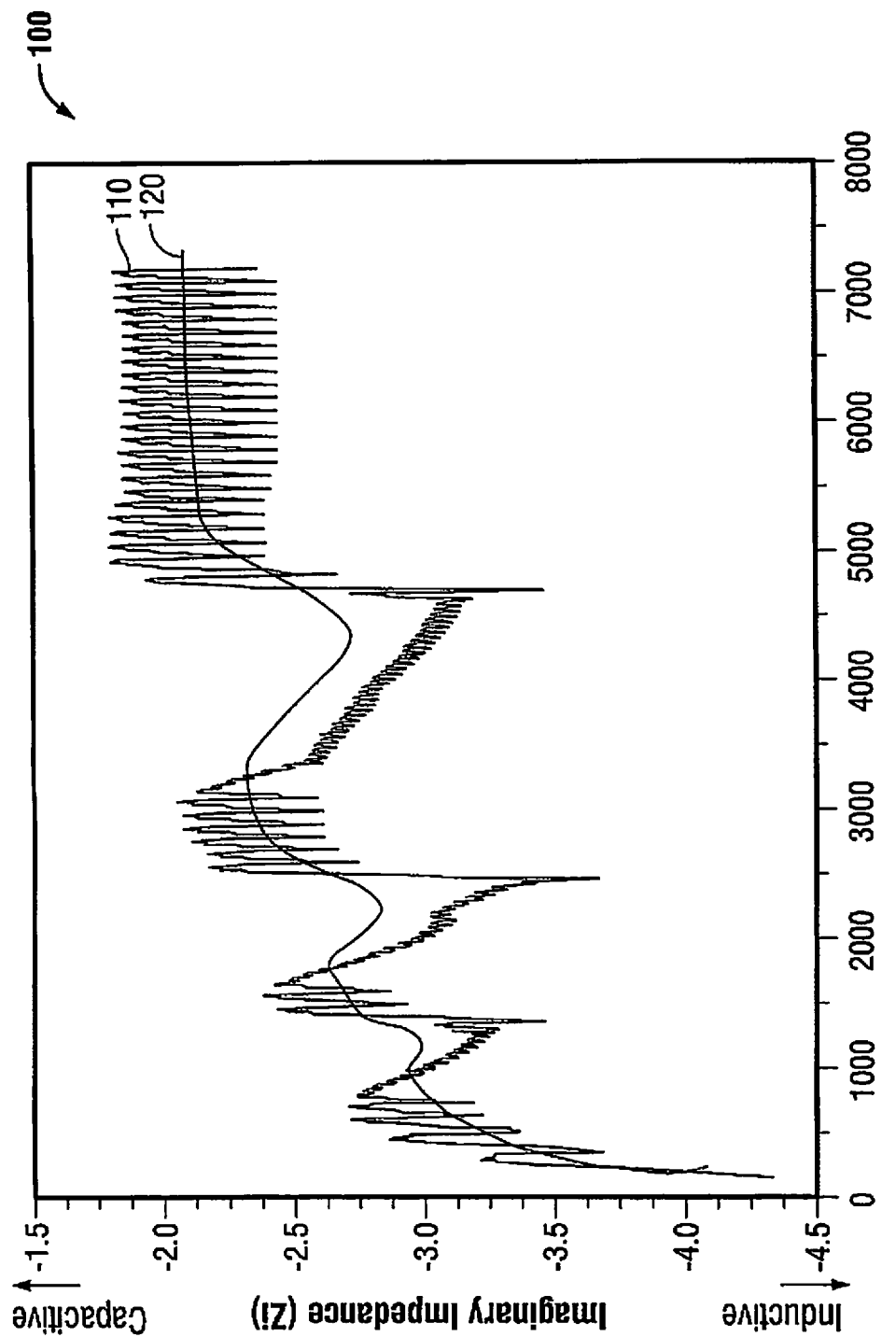
FIG. 7 is a plot of imaginary impedance of tissue during application of electrosurgical energy according to one embodiment of the present disclosure.

With respect to FIG. 4, at the start of application of electrosurgical energy, imaginary impedance starts at a negative value (e.g. from about −5Ω to about −7Ω) and rapidly increases by about 2, this trend is also illustrated in FIGS. 5-7 as discussed in more detail below. The rapid increase in imaginary impedance slows after about 2 to 3 minutes. The trend in imaginary impedance (e.g., rapid increase then slowing after a few minutes) also correlates to the temperature trends observed during ablation. Without being constrained to a particular theory, it is believed that as energy is applied to the tissue, microbubbles form in the intracellular and intercellular space, resulting in low starting imaginary impedance (e.g., more negative, associated with more inductive). As the temperature of the tissue increases, liquid water is driven away from the tissue regions close to phase transition temperature (e.g., 80° C. and above), more microbubbles form, steam bubbles increase in size and these regions become desiccated. The desiccated regions of tissue have higher impedance (e.g., more positive, associated with more positive) and therefore contribute to capacitive impedance. These phenomena are mostly reversible because as the temperature increases and drives the water out, osmotic pressures generate a reverse flow of water. As a result, the tissue seeks a new equilibrium or steady state condition between a desiccated state and a hydrated state to reestablish energy balance.

Once the equilibrium is achieved, the thermal kill zone (e.g., ablation size of the lesion) does not grow significantly. Thus, establishment of equilibrium correlates to the maximum thermal kill zone and may be used to determine whether termination of energy application is appropriate. In other words, monitoring of imaginary impedance allows for determination of the equilibrium, which correlates with maximum thermal kill zone and may therefore, serve as a suitable threshold of intelligent shut-off.

Determination of the equilibrium may be determined by analyzing the slope of the pre-filtered curve 120 or the rate of change of the imaginary impedance. The determination of the slope may be performed at the sensor circuitry 22 and/or the controller 24. A slope of about 0 is believed to be reflective of the establishment of equilibrium, whereas a negative slope corresponds to reduction in energy accumulation within the tissue. Prior to slope analysis, the pre-filtered curve 120 is filtered using single pole recursive filter. Thus, the first filter smoothes out the impedance curve 110 and the recursive filtering detects direction and magnitude of slope changes as described below.

In step 204, the slope of the pre-filtered curve 120 (e.g., rate of change of the imaginary impedance) is determined. According to one embodiment of the present disclosure, the determination of the rate of change may be achieved via single pole recursive filtering that averages a predetermined number of imaginary impedance values to achieve the rate of change value. Any number of impedance filters may be used and are based on the following formula (1):

$$ZfX_n = Zin * A + ZfX_{n-1} * B \tag{1}$$

A and B are dependent on a time constant and may be specified by the user, via the input controls of the generator 20, for each particular impedance filter ZfX. When calculating A and B, the following formulas may be used:

$$B = e^{\wedge}(-1/\text{number of samples});$$

$$A = 1 - B.$$

The sample rate may also be specified by the user for calculating the number of samples. In formula (1), Zin is the new root mean square imaginary impedance value (e.g., $Zi_{RMS}$) just calculated, and $ZfX_{n-1}$ is the filtered imaginary impedance, for the filter number specified by X, from the previous iteration through the loop, and $ZfX_n$ is the new filtered impedance value for the filter number specified by X. In one embodiment, the sample rate for calculating the number of samples may be synchronized with the loop time of the microprocessor 25. Accordingly, within about 5 time constants, the final output of the imaginary impedance filter may be provided that corresponds to the slope of the pre-filtered curve 120. In another embodiment, an initial base imaginary impedance may be used to preload the imaginary impedance filters.

In step 206, the slope of the pre-filtered curve 120 is analyzed. In one embodiment, the slope is analyzed using three regions (e.g., two thresholds). In step 208, it is determined whether the slope is above a first predetermined threshold (e.g., a positive threshold number). In step 210 it is determined whether the slope is between the first threshold and a second predetermined threshold (e.g., a negative number). In step 212, it is determined if the slope is below the second threshold. In another embodiments, a plurality of regions may be utilized based on multiple actions that need to be performed in response to varying slope values. Based on the analysis of the rate of change of the imaginary impedance (e.g., slope) and/or the imaginary impedance, the controller 24 adjusts the output of the generator 20 as discussed in more detail below.

When the slope is above the first threshold, this indicates that the thermal profile is growing and that energy application may continue in step 208. The process then reverts to step 206 to continue slope monitoring and energy application. When the slope is between the first and second thresholds, the thermal profile is in equilibrium which denotes that equilibrium has been reached and an intelligent shut-off process is commenced as shown in step 214. Once it is determined that equilibrium has been reached, a verification is made if a predetermined time delay has expired. This provides a second verification to determine that a substantial portion of the tissue has been treated. The time delay may be user-selectable either by entering a predetermined time value or by selecting one of proposed delay periods. In one embodiment, one of the options may be a time delay corresponding to the shortest time for establishing termination of the procedure and another option may be a time delay corresponding to a conservative treatment regimen that assurance 100% cell kill ratio.

Effects of choosing different time delays is illustrated in FIG. 5, which shows graph 100 of imaginary impedance vs. time (10 samples per second). Imaginary impedance increases initially and then reaches equilibrium as illustrated by the plateau and then decreases significantly. This directs the generator 20 to commence the intelligent shut-off process. If a first time delay "A" (e.g., 5.0 minutes) is selected, the treatment is terminated at the arrow "A." If a second time delay "B" (e.g., 10.8 minutes) is chosen, the treatment is terminated at the arrow "B." The time delay "A" represents a very aggressive time delay, while the second time delay "B" illustrates a very conservative time delay. While there is a 5.8 minute difference between the time delays, the resulting ablation volumes only differed by 0.05 cm in diameter. This illustrates that a longer time delay may not necessarily produce larger ablation volumes and a selection of an appropriate time delay period in certain situations may be user-selectable.

In one embodiment, an intermediate time delay may also be utilized. An intermediate time delay is triggered in step 216 once an equilibrium is reached and the slope detection still continues to make sure that the slope trends do not change. If the slope increases above the first threshold, then energy application resumes. As shown in FIG. 6, which shows graph 100 of imaginary impedance vs. time (10 samples per second), the pre-filtered curve initially reaches equilibrium and then has a slightly negative slope. At this point, the intermediate time delay is triggered and slope interrogation continues. In other words, the process then reverts to step 206 to continue slope monitoring and energy application.

When the slope is less than the second threshold, this denotes that energy application efficiency is decreasing and the procedure should be terminated. This may be caused by proximity to a blood vessel and other obstructions. FIG. 7 shows graph 100 of imaginary impedance vs. time (10 samples per second) having the pre-filtered curve 120 with substantial undulations. Upon encountering negative slopes that are below the second threshold, the process in step 218 terminates the application of energy and/or alerts the user of the decrease in energy application.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for supplying electrosurgical energy to tissue, comprising the steps of:
   measuring at least one of an imaginary impedance and a rate of change of the imaginary impedance of tissue; and
   regulating output of the electrosurgical energy from an electrosurgical generator based on the at least one of the imaginary impedance and rate of change of the imaginary impedance:
   to continue outputting the electrosurgical energy when the rate of change of the imaginary impedance is above a first predetermined threshold;
   to discontinue outputting of the electrosurgical energy when the rate of change of the imaginary impedance is below a second predetermined threshold; and
   to commence termination of the electrosurgical energy when the rate of change of the imaginary impedance is between the first and second predetermined thresholds for a duration of a predetermined time delay.

2. The method according to claim 1, further comprising the step of:
   recursively processing the imaginary impedance to obtain an averaged value of the imaginary impedance.

3. The method according to claim 2, wherein the recursively processing step further includes the step of preloading at least two recursive filters with an initial value of the imaginary impedance.

4. The method according to claim 1, wherein the regulating step further includes the step of:
   restarting application of the electrosurgical energy when the rate of change of the imaginary impedance is above the first predetermined threshold during the predetermined time delay.

5. A method for supplying electrosurgical energy to tissue, comprising the steps of:
   measuring an imaginary impedance and a rate of change of the imaginary impedance of tissue; and
   regulating the electrosurgical energy based on at least one of the imaginary impedance and rate of change of the imaginary impedance, wherein the regulating step further includes the step of:
   comparing the rate of change of the imaginary impedance with a first predetermined threshold and a second predetermined threshold;
   continuing application of the electrosurgical energy to tissue when the rate of change of the imaginary impedance is above the first predetermined threshold;

discontinuing application of the electrosurgical energy to tissue when the rate of change of the imaginary impedance is below the second predetermined threshold; and terminating the electrosurgical energy when the rate of change of the imaginary impedance is between the first and second predetermined thresholds for a duration of a predetermined time delay.

6. The method according to claim 5, further comprising the step of:

recursively processing the imaginary impedance to obtain an averaged value of the imaginary impedance.

7. The method according to claim 5, wherein the regulating step further includes the step of:

restarting application of the electrosurgical energy when the rate of change of the imaginary impedance is above the first predetermined threshold during the predetermined time delay.

* * * * *